US011510979B2

(12) United States Patent
Gill et al.

(10) Patent No.: US 11,510,979 B2
(45) Date of Patent: Nov. 29, 2022

(54) POLLEN GRAINS FOR TREATMENT OF PEANUT AND OTHER ALLERGIES

(71) Applicant: Texas Tech University System, Lubbock, TX (US)

(72) Inventors: Harvinder Singh Gill, Lubbock, TX (US); Akhilesh Shakya, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 124 days.

(21) Appl. No.: 16/753,612

(22) PCT Filed: Oct. 2, 2018

(86) PCT No.: PCT/US2018/053852
§ 371 (c)(1),
(2) Date: Apr. 3, 2020

(87) PCT Pub. No.: WO2019/070631
PCT Pub. Date: Apr. 11, 2019

(65) Prior Publication Data
US 2020/0289644 A1 Sep. 17, 2020

Related U.S. Application Data

(60) Provisional application No. 62/568,846, filed on Oct. 6, 2017.

(51) Int. Cl.
*A61K 39/36* (2006.01)
*A61P 37/08* (2006.01)
*A61K 39/00* (2006.01)
*A61K 39/35* (2006.01)

(52) U.S. Cl.
CPC .............. *A61K 39/36* (2013.01); *A61K 39/35* (2013.01); *A61P 37/08* (2018.01); *A61K 2039/542* (2013.01); *A61K 2039/545* (2013.01); *A61K 2039/55511* (2013.01)

(58) Field of Classification Search
None
See application file for complete search history.

(56) References Cited

FOREIGN PATENT DOCUMENTS

| WO | 2005/046704 A1 | 5/2005 |
| WO | 2009/077749 A1 | 6/2009 |
| WO | 2014/062566 A1 | 4/2014 |

OTHER PUBLICATIONS

Kuby Immunology, 4th Edition, Chapter 18, "Vaccines," pp. 449-465 (2001).*
Mukherjee et al. 'Allergic Asthma: Influence of Genetic and Environmental Factors.' J. Biol. Chem. 286(38):32883-32889, 2011.*
Kurucz et al. 'Current Animal Models of Bronchial Asthma.' Curr. Pharm. Des. 12:3175-3194, 2006.*
Kristiansen et al. 'Allergen immunotherapy for the prevention of allergy: A systematic review and meta-analysis.' Pediatr Allergy Immunol. Feb. 2017;28(1):18-29. doi: 10.1111/pai.12661. Epub Dec. 12, 2016.*
Martignago et al. 'Preventive actions of allergen immunotherapy: the facts and the effects in search of evidence.' Clin Mol. Allergy 2017; 15: 13. Published online Jun. 15, 2017. doi: 10.1186/s12948-017-0070-7.*
Caubet et al. 'Current understanding of egg allergy.' Pediatr Clin North Am. Author manuscript; available in PMC Apr. 1, 2012.*
Reboucas et al. 'Immunogenicity of Peanut Proteins Containing Poly(Anhydride) Nanoparticles.' Clinical and Vaccine Immunology 21(8):1106-1112, 2014.*
Larsen, J.N. et al. "Allergy immunotherapy: the future of allergy treatment" Drug Discov Today, 21 (2016) 26-37.
Lee, H.J. et al. "Acidification of stratum corneum prevents the progression from atopic dermatitis to respiratory allergy" Exp. Dermatol., (2016).
Li, W. et al. "Prevention of oral food allergy sensitization via skin application of food allergen in a mouse model" Allergy, 67 (2012) 622-629.
Mehta, H. et al. "Growth and Nutritional Concerns in Children with Food Allergy" Current opinion in allergy and clinical immunology, 2013. 13(3): p. 275-279.
Meyer, R. et al. "Malnutrition in children with food allergies in the UK" Journal of Human Nutrition and Dietetics, 2014. 27(3): p. 227-235.
Naclerio, R.M. "The effect of antihistamines on the immediate allergic response: a comparative review" Otolaryngol Head Neck Surg, 108 (1993) 723-730.
Narisety, S.D. et al. "A randomized, double-blind, placebo-controlled pilot study of sub/ingua/ versus oral immunotherapy for the treatment of peanut allergy." Journal of Allergy and Clinical Immunology, 2015. 135(5): p. 1275-1282e6.
Nelson, H.S. et al. "Treatment of anaphylactic sensitivity to peanuts by immunotherapy with injections of aqueous peanut extract" J Allergy Clin Immunol, 1997. 99(6 Pt 1): p. 744-51.
Nurmatov, U. et al. "Allergen-specific oral immunotherapy for peanut allergy" Cochrane Database Syst Rev, 2012(9) : p. CD009014.
O'Garra, A. et al. "IL-10-producing and naturally occurring CD4+ Tregs: limiting collateral damage" J Clin Invest, 2004. 114(10): p. 1372-8.
Oppenheimer, J.J. et al. "Treatment of peanut allergy with rush immunotherapy" J Allergy Clin Immunol, 1992. 90(2): p. 256-62.
Pajno, G.B. et al. "Oral Immunotherapy for Treatment of Immunoglobulin E-Mediated Food Allergy: The Transition to Clinical Practice" Pediatric Allergy, Immunology, and Pulmonology, 2014. 27(2): p. 42-50.

(Continued)

*Primary Examiner* — Nora M Rooney
(74) *Attorney, Agent, or Firm* — Edwin S. Flores; Daniel J. Chalker; Chalker Flores, LLP

(57) ABSTRACT

The present invention includes composition and methods for composition for the oral delivery of a therapeutic agent that reduces, desensitizes, or prevents food, respiratory and other allergies. First pollen is cleaned to remove naturally-occurring allergic plant proteins to form a cleaned pollen and a therapeutically effective amount of an allergen is introduced into the cleaned pollen. The allergen-loaded cleaned pollen is delivered to a subject in need of therapy.

25 Claims, 20 Drawing Sheets

Specification includes a Sequence Listing.

(56) References Cited

OTHER PUBLICATIONS

Platts-Mills, T.A. "The allergy epidemics: 1870-2010" J Allergy Clin Immunol, 136 (2015) 3-13.
Richert, J.H. "Failure to Develop Saecoidosis after the Oral Ingestion of Pine Pollen" American Review of Respiratory Disease, 1959. 80(5): p. 760.
Sampson, H.A. et al. "Food allergy: a practice parameter update—2014" J Allergy Clin Immunol, 2014. 134(5): p. 1016-25 e43.
Sampson, H.A. et al. "Peanut Oral Immunotherapy: Is It Ready for Clinical Practice?" The Journal of Allergy and Clinical Immunology: In Practice, 2013. 1(1): p. 15-21.
Shaw, G., The chemistry of sporopollenin, in Sporopollenin, P.R. Grant, M. Muir, P.V. Gijzel, and G. Shaw, Editors. 1971, Academic Press, London.
Sicherer et al. "Clinical Features of Acute Allergic Reactions to Peanut and Tree Nuts in Children" (1998). Pediatrics 102(1), p.e6.
Sicherer et al. "Peanut and soy allergy: a clinical and therapeutic dilemma" (2000). Allergy 55(6), pp. 515-521.
Sicherer, S.H. et al. "US prevalence of self-reported peanut, tree nut, and sesame allergy: 11-year follow-up" Journal of Allergy and Clinical Immunology, 2010. 125(6): p. 1322-1326.
Skolnick, H.S. et al. "The natural history of peanut allergy" Journal of Allergy and Clinical Immunology, 2001. 107(2): p. 367-374.
Taudorf, E. et al., Oral administration of grass pollen to hay fever patients. An efficacy study in oral hyposensitization. Allergy, 1985. 40(5): p. 321-35.
Taudorf, E. et al. "Oral immunotherapy in birch pollen hay fever" J Allergy Clin Immunol, 1987. 80(2): p. 153-61.
Taylor et al. "A consensus protocol for the determination of the threshold doses for allergenic foods: how much is too much?" (2004). Clin Exp. Allergy 34, pp. 689-695.
Valenta, R. et al. "Allergen-specific immunotherapy: from therapeutic vaccines to prophylactic approaches" J Intern Med, 272 (2012) 144-157.
Valovirta, E. et al. "G.A.P. investigators, Design and recruitment for the GAP trial, investigating the preventive effect on asthma development of an SQ-standardized grass allergy immunotherapy tablet in children with grass pollen-induced allergic rhinoconjunctivitis" Clin Ther, 33 (2011) 1537-1546.
Vickery, B.P. et al. "Early oral immunotherapy in peanut-allergic preschool children is safe and highly effective" J Allergy Clin Immunol, 2017. 139(1): p. 173-181 e8.
Volkheimer, G. "Passage of particles through the wall of the gastrointestinal tract" Environ Health Perspect, 1974. 9: p. 215-25.
Volkheimer, G. et al. "Persorption of metallic iron particle" Gut, 1969. 10(1): p. 32-3.
Walkner, M. et al. "Quality of Life in Food Allergy Patients and Their Families" Pediatric Clinics of North America, 2015. 62(6): p. 1453-1461.
Wittborn, J. et al. "Nanoscale Similarities in the Substructure of the Exines of Fagus pollen grains and lycopodium spores." Annals of Botany, 1998. 82(2): p. 141-145.
Wittborn, J. et al. "Substructure of spore and pollen grain exines in Lycopodium, A/nus, Betu/a, Fagus and Rhododendron—Investigation with Atomic Force and Scanning Tunnelling Microscopy" Grana, 1996. 35(4): p. 185-198.
Wohrl, S. et al. "Underestimation of allergies in elderly patients" Lancet, 2004. 363(9404): p. 249.
Wood, RA. "Food allergen immunotherapy: Current status and prospects for the future" J Allergy Clin Immunol, 2016. 137(4): p. 973-82.
Wood, RA., "Oral Immunotherapy for Food Allergy." J Investig Allergol Clin Immunol, 2017.
Zhou et al. "Allergen Nomenclature Sub-Committee of the International Union of Immunological Societies" (2013). International Journal of Food Science, V. 2013, Article ID 909140.
Zolkipli, Z. et al. "Randomized controlled trial of primary prevention of atopy using house dust mite allergen oral immunotherapy in early childhood" J Allergy Clin Immunol, 136 (2015) 1541-1547 e1541-1511.
Akdis, C.A. et al. "Mechanisms of allergen-specific immunotherapy" J Allergy Clin Immunol, 2011. 127(1): p. 18-27.
Akdis, C.A. et al. "Mechanisms of immune tolerance to allergens: role of/ L-10 and Tregs" J Clin Invest, 2014. 124(11): p. 4678-80.
Allakhverdi, Z. et al. "Adjuvant activity of pollen grains". Allergy, 2005, vol. 60, No. 9, pp. 1157-1164.
Anagnostou, K. et al. "Assessing the efficacy of oral immunotherapy for the desensitisation of peanut allergy in children (STOP II): a phase 2 randomised controlled trial" The Lancet. 383(9925): p. 1297-1304.
Anagnostou, K. et al. "Efficacy and safety of high-dose peanut oral immunotherapy with factors predicting outcome" Clinical & Experimental Allergy, 2011. 41(9): p. 1273-1281.
Atwe, S.U. et al. "Pollen grains for oral vaccination" J Control Release, 2014. 194: p. 45-52.
Bernstein, T.B. et al. "Oral ragweed pollen therapy clinical results of experiments on gastrointestinal absorption." Arch Intern Med (Chic), 1938. 62(2): p. 297-304.
Blumchen, K. et al. "Oral peanut immunotherapy in children with peanut anaphylaxis" Journal of Allergy and Clinical Immunology, 2010. 126(1): p. 83-91.e1.
Bollinger, M.E. et al. "The impact of food allergy on the daily activities of children and their families" Annals of Allergy, Asthma & Immunology, 2006. 96(3): p. 415-421.
Boyce, J.A. et al. "Guidelines for the diagnosis and management of food allergy in the United States: report of the NIAID-sponsored expert panel" J Allergy Clin Immunol, 2010. 126(6 Suppl): p. S1-58.
Branum, A.M. et al. "Food Allergy Among Children in the United States" Pediatrics, 2009. 124(6): p. 1549-1555.
Bukantz, S.C. et al. "Adverse effects and fatalities associated with subcutaneous allergen immunotherapy" Clin Allergy Immunol, 21 (2008) 455-468.
Campbell, D.E. et al. "Fifty years of allergy: 1965-2015" J Paediatr Child Health, 51 (2015) 91-93.
Chafen, J. et al., "Diagnosing and managing common food allergies: A systematic review" JAMA, 2010. 303(18): p. 1848-1856.
Cox, L. et al. "Allergen immunotherapy: a practice parameter third update" J Allergy Clin Immunol, 127 (2011) 51-55.
D'Amato, G. et al. "Treating severe allergic asthma with anti-IgE monoclonal antibody (omalizumab): a review" Multidiscip Respir Med, 9 (2014) 23.
de Leon et al. "Immunological analysis of allergenic cross-reactivity between peanut and treenuts" (2003). Clin. Exp. Allergy 33(9), pp. 1273-1280.
Deol, S. et al. "Current opinion and review on peanut oral immunotherapy" Hum Vaccin Immunother, 2014. 10(10): p. 3017-21.
Diego-Taboada, A. et al. "Hollow pollen shells to enhance drug delivery" Pharmaceutics, 2014. 6(1): p. 80-96.
Diesner, S.C. et al. "Food Allergy: Only a Pediatric Disease?" Gerontology, 2011. 57(1): p. 28-32.
Du, Y. Z. et al. "Preparation and characterization of biotinylated and enzyme-immobilized heterobifunctional latex particles as nanobio devices." Journal of Polymer Science Part A: Polymer Chemistry, 2005. 43(3): p. 562-574.
Feinberg, S.M. et al. "Oral Pollen Therapy in Ragweed Poll/Nosis a Cooperative Study" The Journal of the American Medical Association, 1940. 115(1): p. 23-29. [abstract].
Fleischer, D.M. et al. "The natural progression of peanut allergy: Resolution and the possibility of recurrence" Journal of Allergy and Clinical Immunology, 2003. 112(1): p. 183-189.
Frew, A.J. "Allergen immunotherapy" J Allergy Clin Immunol, 125 (2010) S306-313.
Fujita, H. et al. "Mechanisms of allergen-specific immunotherapy" Clin Transl Allergy, 2 (2012) 2.
Galli, S.J. et al. "IgE and mast cells in allergic disease" Nat Med, 18 (2012) 693-704.

(56) References Cited

OTHER PUBLICATIONS

Heslop-Harrison, Y. et al. "Structural and functional variation in pollen intines, in Pollen and Spores" S. Blackmore and S. Barnes, Editors. 1991, Clarendon Press: Oxford, p. 331-343.

Hessenberger, M. et al. "Transcutaneous delivery of CpG-adjuvanted allergen via laser-generated micropores", Vaccine, 31 (2013) 3427-3434.

Hofmann, A.M. et al. "Safety of a peanut oral immunotherapy protocol in children with peanut allergy" J Allergy Clin Immunol, 2009. 124(2): p. 286-91, 291.e1-6.

Holt, P.G. et al. "Prophylactic use of sublingual allergen immunotherapy in high-risk children: a pilot study" J. Allergy Clin. Immunol., 132 (2013) 991-993 e991.

Hourihane, J.O.B. et al. "Resolution of peanut allergy: case-control study" BMJ : British Medical Journal, 1998. 316 (7140): p. 1271-1275.

Incorvaia, C. "Preventive capacity of allergen immunotherapy on the natural history of allergy" J Prev Med Hyg, 54 (2013) 71-74.

Incorvaia, C. et al. "Specific immunotherapy by the sublingual route for respiratory allergy" Allergy Asthma Clin. Immunol., 6 (2010) 29.

International Search Report and Written Opinion, PCT/US2018/053852 [ISA/AU] dated Jan. 31, 2019.

Jacobsen, L. et al. "Specific immunotherapy has long-term preventive effect of seasonal and perennial asthma: 10-year follow-up on the PAT study" Allergy, 62 (2007) 943-948.

Jones, S.M. et al. "Clinical efficacy and immune regulation with peanut oral immunotherapy" Journal of Allergy and Clinical Immunology, 2009. 124(2): p. 292-300.e97.

Jorde, W. et al. "Zur Persorption Von Pollen und Spoken Durch die Intake Darmschleimhaut" Allergy, 1974. 29(3): p. 165-175.

Kanaoka, M.M. et al. "Peptide signaling in pollen tube guidance" Current Opinion in Plant Biology, 2015. 28: p. 127-136.

Kim, J. et al. "Nanostructures for enzyme stabilization" Chemical Engineering Science, 2006. 61(3): p. 1017-1026.

Kim, S.J. et al. "Preventive effects of oral tolerance on allergic inflammation and airway remodeling in a murine model" Am. J. Rhinol. Allergy, 27 (2013) e11-16.

\* cited by examiner

SEQUENCE LISTING

```
<160> NUMBER OF SEQ ID NOS: 28

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1

Pro Gly Gln Phe Glu Asp Phe Phe
1               5
```

```
<210> SEQ ID NO 2
<211> LENGTH: 8
<212> TYPE: PRT
<213> ORGANISM: Artificial Sequence
<220> FEATURE:
<223> OTHER INFORMATION: Synthetic peptide

<400> SEQUENCE: 2

Tyr Leu Gln Gly Phe Ser Arg Asn
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic peptide

<400> SEQUENCE: 3

Phe Asn Ala Glu Phe Asn Glu Ile Arg Arg
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Synthetic peptide

<400> SEQUENCE: 4

Gln Glu Glu Arg Gly Gln Arg Arg
1               5

<210> SEQ ID NO 5
<211> LENGTH: 10
<212> TYPE: PRT
<213> ORGANISM: Artificial Sequence
<220> FEATURE:
<223> OTHER INFORMATION: Synthetic peptide

<400> SEQUENCE: 5

Asp Ile Thr Asn Pro Ile Asn Leu Arg Glu
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide

<400> SEQUENCE: 6

Asn Asn Phe Gly Lys Leu Phe Glu Val Lys
1               5                   10

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide

<400> SEQUENCE: 7

Gly Asn Leu Glu Leu Val
1               5
```

```
<210> SEQ ID NO 8
<211> LENGTH: 10
<212> TYPE: PRT
<213> ORGANISM: Artificial Sequence
<220> FEATURE:
<223> OTHER INFORMATION: Synthetic peptide

<400> SEQUENCE: 8

Arg Arg Tyr Thr Ala Arg Leu Lys Glu Gly
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic peptide

<400> SEQUENCE: 9

Glu Leu His Leu Leu Gly Phe Gly Ile Asn
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic peptide

<400> SEQUENCE: 10

His Arg Ile Phe Leu Ala Gly Asp Lys Asp
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic peptide

<400> SEQUENCE: 11

Ile Asp Gln Ile Glu Lys Gln Ala Lys Asp
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic peptide

<400> SEQUENCE: 12

Lys Asp Leu Ala Phe Pro Gly Ser Gly Glu
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic peptide

<400> SEQUENCE: 13

Lys Glu Ser His Phe Val Ser Ala Arg Pro
1               5                   10
```

```
<210> SEQ ID NO 14
<211> LENGTH: 25
<212> TYPE: PRT
<213> ORGANISM: Artificial Sequence
<220> FEATURE:
<223> OTHER INFORMATION: Synthetic peptide

<400> SEQUENCE: 14

Asn Glu Gly Val Ile Val Lys Val Ser Lys Glu His Val Glu Glu Leu
1               5                   10                  15

Thr Lys His Ala Lys Ser Val Ser Lys
            20                  25

<210> SEQ ID NO 15
<211> LENGTH: 10
<212> TYPE: PRT
<213> ORGANISM: Artificial Sequence
<220> FEATURE:
<223> OTHER INFORMATION: Synthetic peptide

<400> SEQUENCE: 15

His Ala Ser Ala Arg Gln Gln Trp Glu Leu
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic peptide

<400> SEQUENCE: 16

Gln Trp Glu Leu Gln Gly Asp Arg Arg Cys
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic peptide

<400> SEQUENCE: 17

Asp Arg Arg Cys Gln Ser Gln Leu Glu Arg
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide

<400> SEQUENCE: 18

Leu Arg Pro Cys Glu Gln His Leu Met Gln
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic peptide

<400> SEQUENCE: 19

Lys Ile Gln Arg Asp Glu Asp Ser Tyr Glu
1               5                   10
```

```
<210> SEQ ID NO 20
<211> LENGTH: 10
<212> TYPE: PRT
<213> ORGANISM: Artificial Sequence
<220> FEATURE:
<223> OTHER INFORMATION: Synthetic peptide

<400> SEQUENCE: 20

Tyr Glu Arg Asp Pro Tyr Ser Pro Ser Gln
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic peptide

<400> SEQUENCE: 21

Ser Gln Asp Pro Tyr Ser Pro Ser Pro Tyr
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic peptide

<400> SEQUENCE: 22

Asp Arg Leu Gln Gly Arg Gln Gln Glu Gln
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic peptide

<400> SEQUENCE: 23

Lys Arg Glu Leu Arg Asn Leu Pro Gln Gln
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic peptide

<400> SEQUENCE: 24

Gln Arg Cys Asp Leu Asp Val Glu Ser Gly
1               5                   10

<210> SEQ ID NO 25
<211> LENGTH: 15
<212> TYPE: PRT
<213> ORGANISM: Artificial Sequence
<220> FEATURE:
<223> OTHER INFORMATION: Synthetic peptide

<400> SEQUENCE: 25

Ile Glu Thr Trp Asn Pro Asn Asn Gln Glu Phe Glu Cys Ala Gly
1               5                   10                  15
```

```
<210> SEQ ID NO 26
<211> LENGTH: 15
<212> TYPE: PRT
<213> ORGANISM: Artificial Sequence
<220> FEATURE:
<223> OTHER INFORMATION: Synthetic peptide

<400> SEQUENCE: 26

Gly Asn Ile Phe Ser Gly Phe Thr Pro Glu Phe Leu Ala Gln Ala
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic peptide

<400> SEQUENCE: 27

Val Thr Val Arg Gly Gly Leu Arg Ile Leu Ser Pro Asp Arg Lys
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic peptide

<400> SEQUENCE: 28

Asp Glu Asp Glu Tyr Glu Tyr Asp Glu Glu Asp Arg Arg Arg Gly
1               5                   10                  15
```

POLLEN GRAINS FOR TREATMENT OF PEANUT AND OTHER ALLERGIES

CROSS-REFERENCE TO RELATED APPLICATIONS

This application is the National Stage of International Application No. PCT/US2018/053852, filed on Oct. 2, 2018 claiming the priority of U.S. Provisional Application No. 62/568,846, filed on Oct. 6, 2017, the content of each of which is incorporated by reference herein.

Incorporation-by-Reference of Materials Filed on Compact Disc

The present application includes a Sequence Listing which has been submitted in ASCII format via EFS-Web and is hereby incorporated by reference in its entirety. Said ASCII copy, created on Oct. 1, 2018, is named TECH1156US SeqListing.txt and is 6, kilo bytes in size.

STATEMENT OF FEDERALLY FUNDED RESEARCH

This invention was made with government support under 1DP2HD075691-01 awarded by the National Institutes of Health. The government has certain rights in the invention.

TECHNICAL FIELD OF THE INVENTION

The present invention relates in general to the field of reducing or preventing food and respiratory allergies, and more particularly, to a novel pollen composition for the treatment of peanut and other allergies.

BACKGROUND OF THE INVENTION

Without limiting the scope of the invention, its background is described in connection with food allergies and respiratory allergies.

Peanut allergy is a life-threatening condition. About 1% of the US population (~3 million people)(1,2) has peanut allergies, and this number has tripled since 1990s (3,4). Peanut allergy occurs early in life and is life-long because only 20% of children may outgrow their peanut allergy (5-7). Peanut allergy has no FDA-approved treatment. Allergy shots for food allergy are not approved because they carry high risk and have high adverse reaction-rates (8,9). Strict avoidance, and a peanut-free diet is the only option available to manage peanut allergies (10). Patients are also advised to carry an epinephrine injection to mitigate anaphylaxis, which can occur due to accidental peanut exposure. Adherence to a peanut-free diet imposes severe limitations on the lifestyle of the patient and their families (11), and reduces their quality of living (12). Importantly, restricted food diets in children can lead to nutritional deficiencies (13,14). Although food allergies are often considered a disease affecting the children, their occurrence in the elderly is also high and is often underestimated (15,16).

Peanut allergy is associated with an abnormal immune response to peanut proteins and it is mediated by peanut specific IgE antibodies (17,18). Allergic reaction to peanut in food can produce diverse symptoms including skin rashes, gastrointestinal reactions such as pain and vomiting, and even a severe life-threatening anaphylactic reaction (17). Peanut oral immune-therapy (OIT) is relatively new and experimental (19), and it aims to modulate this aberrant IgE response. The first open-label trial for peanut OIT was published in 2009 (20,21). The published (19,22,23) protocols for peanut OIT (and food OIT in general) typically involve oral delivery of peanut flour/protein or extract in: (i) a rapid/rush dose escalation phase lasting one day (peanut protein dose increased from about 100 μg to 50 mg), (ii) a gradual dose buildup phase lasting many months (peanut protein dose increased to hundreds and thousands of milligram), and (iii) maintenance phase lasting months to years (peanut protein dose maintained at several thousand milligram).

Current peanut OIT protocols require daily ingestion of peanut, and the dose is continuously increased to thousands of milligrams of peanut protein. Adverse events such as abdominal pain, vomiting, upper respiratory reactions (sneezing and congestion), and skin rashes/hives are very common, especially during the initial rush dose escalation from micrograms to tens of milligram in a single day (20), and the dose buildup phase when the peanut dose is raised from tens to thousands of milligrams (24). In one study a direct correlation was observed between asthma and peanut OIT, wherein it was found that asthmatic patients experienced respiratory adverse events (20). Patients have been reported to dropout from peanut clinical OIT trials due to adverse events (25-28). Thus, not only is peanut OIT prolonged, but no significant treatment benefits have been obtained so far, and peanut OIT is currently not recommended for clinical use.

Appearance of airway allergies is a common public health issue and their prevalence is steadily on the rise worldwide (29, 30). Airway allergies are largely type 1 hypersensitivity reactions, and they are characterized by elevated levels of systemic allergen-specific IgE antibodies and hyperreactivity of the airway tract (31). Medications such as anti-IgE therapy, and anti-histamines, which can be administered orally or systemically via injections are available for short term relief (32, 33). However, allergen specific immunotherapy (ASI) is the only approach to treat allergies permanently (34). ASI is recommended for allergy patients who have allergen-specific IgE in their serum (34, 35). In conventional ASI involving subcutaneous allergy immunotherapy (SCIT), multiple injections of increasing doses of a specific allergen are given to the patient until a therapeutic level is reached. The treatment is time consuming because it spans many years, is painful, and is linked to potential systemic reactions, or occasional anaphylaxis (36, 37).

The current form of SCIT is only initiated once a patient has developed allergies. Thus, to halt the allergy pandemic, recently a true mode of vaccination in the form of 'prophylaxis/preventive allergy treatment' has come into light (38, 39). Preventive vaccination can begin in healthy individuals even with a negative skin prick test (i.e., have not yet developed allergen-specific IgE antibodies), but who are genetically susceptible to allergy development. This immunomodulation starts in early childhood to block allergy development in later phases of life, and is thus termed as 'primary prevention' (39). Few case studies have been reported on primary preventive allergy immunomodulation. A dust mite allergy study showed the efficacy of preventive immunomodulation in 111 infants who were less than a year old and received an oral dose of the house dust mite (HDM) extract twice daily for 12 months (40). As a result, although the risk of allergy development to common allergens was reduced, but allergy development to HDM was not blocked (40). An important milestone-observation from this study was that the exposure of infants to HDM who were yet not sensitized to the HDM allergen did not cause an increase in their HDM-specific or non-specific allergies, suggesting that such immunomodulatory treatments are potentially safe.

Another form of allergy prevention is 'secondary prevention', which has multiple connotations: (i) to block disease development in already sensitized individuals, for example to prevent development of asthma if the patient is already allergic to airway allergens but does not yet have asthma, and, (ii) to prevent development of a second sensitization if a patient is already allergic to one allergen. For instance, allergic rhinoconjunctivitis is a risk factor for asthma development, meaning patients with allergic rhinoconjunctivitis could develop asthma over time. It was recently shown that a three year long subcutaneous ASI in patients with allergic rhinoconjunctivitis to grass and/or birch pollen reduced their risk of asthma development during treatment and two years after discontinuation of treatment (41). In another study over 800 children between the ages of 5-12 y and with grass-allergen-induced rhinoconjunctivitis but with no signs of asthma were administered grass allergen immunotherapy tablets sublingually (46). The objective was to test if this could reduce or prevent asthma development during the three years of treatment and two years post-treatment. After immunotherapy a significantly fewer number of children experienced asthma or used asthma medication, and this effect sustained for two years after end of treatment (43). The trial also demonstrated that allergic rhinoconjunctivitis symptoms were also significantly reduced.

Allergy preventive studies have thus far used the conventional SCIT route, the oral route, or the sublingual route, at preclinical and clinical levels (40, 42, 44-47). However the problem of holding the formulation under the tongue for few minutes by infants in sublingual immunotherapy is a concern. For example, a pilot study for dust mite allergy prevention in infants was terminated early without any major conclusions due to the inability to train infants to hold the liquid formulation under the tongue for two minutes (48). The SCIT shots are painful, and the efficacy of the oral route is not as good as the SCIT route (49).

A document was developed by the Joint Task Force on Practice Parameters, which represents the American Academy of Allergy, Asthma & Immunology (AAAAI); the American College of Allergy, Asthma & Immunology (ACAAI); and the Joint Council of Allergy, Asthma & Immunology (JCAAI) (43). The Joint Task Force objective was to optimize the practice of allergen immunotherapy for patients with allergic diseases. This parameter was intended to establish guidelines for the safe and effective use of allergen immunotherapy while reducing unnecessary variation in immunotherapy practice. This document states that: "Administration of pollen allergen extracts through the oral route reduces symptoms caused by natural pollen exposure, but the dose required is much greater compared with that required through the subcutaneous route; gastrointestinal side effects are frequent. The oral approach has been largely abandoned for inhalant allergens but has been pursued for treatment of food allergy in children."

This clearly shows that the oral route for treatment of respiratory allergens is not normal, and thus the claims set forth in this patent are not anticipated from the prior art or those skilled in practicing allergen immunotherapy in clinics.

SUMMARY OF THE INVENTION

In one embodiment, the present invention includes a composition for the oral delivery of a therapeutic agent that reduces, desensitizes, or prevents food, respiratory or other allergies, comprising: a pollen cleaned to remove naturally-occurring allergic plant proteins; and a therapeutically effective amount of an allergen loaded into the cleaned pollen, wherein the allergen is in an amount that enhances the production of antibodies against the allergen. In one aspect, the cleaned pollen is stabilized during processing or storage in a vehicle, or both. In another aspect, the composition is adapted for prophylactic use as a preventive vaccine. In another aspect, the composition is adapted into an immunogen to treat an allergy via immunotherapy. In another aspect, the cleaned pollen is an adjuvant. In another aspect, the composition comprises an allergen and an adjuvant. In another aspect, the allergen is a food allergy allergen to a groundnut, peanut, milk, egg, tree nut, seed, fish, shellfish, crustacean, cereal, legume allergy, hazelnut, cashew, walnut, pecan, brazil nut, macadamia, chestnut, pistachio, coconut, almond, sesame, soy, kidney bean, black bean, common bean, chickpea, pea, cow pea, lentil or lupine allergy or a mustard seed allergy, or a combination thereof. In another aspect, the allergen is peanut allergen that comprises Ara h1, Ara h2, Ara h3, Ara h4, Ara h5, Ara h6, Ara h7, Ara h8, Ara h9, Ara h10, Ara h11, Ara h12, Ara h13, a peptide fragment thereof, or a combination thereof. In another aspect, the allergen is a plant, pollen, animal, arthropod, insect, fungus, or venom allergen. In another aspect, the allergen is an aeroallergen, pollen allergen, animal allergen, dust mite allergen, cockroach allergen, or mold or fungi allergen, Hymenoptera allergen, or combinations thereof. In another aspect, the allergen is an extract derived from the allergic source material, or purified from the extract, or synthesized chemically or biologically, and is whole or a fragment thereof of the allergen. In another aspect, the allergen can be a mixture of two or more allergens in a ratio from 0.001:100 to 100:0.001. In another aspect, the amount of the allergen loaded into the cleaned pollen in an amount that is below the threshold that triggers an allergic response to the allergen. In another aspect, the allergen is in, on, about, or a film coated on the cleaned pollen or a combination thereof. In another aspect, an opening in the cleaned pollen is at least partially or fully closed with a biodegradable polymer. In another aspect, the composition further comprises one or more adjuvants in any size, shape, form or physical state introduced in, on, or about the cleaned pollen or a combination thereof that improve the immune response against the allergen. In another aspect, the cleaned pollen are ragweed pollen. In another aspect, the allergen amount is less than about 1 gram, more preferably less than about 100 mg, more preferably less than about 1 mg, more preferably less than about 500 microgram, and more preferably less than about 100 microgram. In another aspect, the allergen is a peanut allergen and the amount of the peanut allergen is between 1 nanogram to 1 gram per dose. In another aspect, a dosage of pollen is about 1 grams of pollen per dose, more preferably about 500 mg per dose, more preferably about 100 mg per dose, more preferably about 10 mg per dose, or more preferably less than 10 mg per dose. In another aspect, the composition has improved organoleptic properties when compared to allergen alone. In another aspect, a desensitization to the allergen in a subject is by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, about 70%, about 75%, at least about 80%, at least about 85%, or at least about 90% as compared to the subject prior to commencing the treatment, a subject receiving a placebo or a subject not receiving the treatment.

In another embodiment, the present invention includes a method for making a composition for delivery of a therapeutic agent that reduces, desensitizes, or prevents food, respiratory or other allergies, the composition comprising: cleaning a pollen to remove naturally-occurring allergic protein or fragment thereof to form a cleaned pollen; enclosing a therapeutically effective amount of an allergen in the cleaned pollen; and providing to a subject in need of immunotolerance with a therapeutically effective amount of an allergen in or on the pollen sufficient to induce immune tolerance to the allergen. In one aspect, the method further comprises the step of stabilizing the composition during processing for storage. In another aspect, the method further comprises adapting the composition for prophylactic use as a preventive vaccine. In another aspect, the method further comprises adapting the composition for therapeutic use as a vaccine to treat allergy via immunotherapy. In another aspect, the method further comprises adapting the composition for oral, subcutaneous, intranasal, or intrapulmonary administration. In another aspect, the cleaned pollen is an adjuvant. In another aspect, the composition comprises an allergen and an adjuvant. In another aspect, the allergen is a food allergy allergen to a groundnut, peanut, milk, egg, tree nut, seed, fish, shellfish, crustacean, cereal, legume allergy, hazelnut, cashew, walnut, pecan, brazil nut, macadamia, chestnut, pistachio, coconut, almond, sesame, soy, kidney bean, black bean, common bean, chickpea, pea, cow pea, lentil or lupine allergy or a mustard seed allergy, or a combination thereof. In another aspect, the allergen is peanut allergy allergen that comprises Ara h1, Ara h2, Ara h3, Ara h4, Ara h5, Ara h6, Ara h7, Ara h8, Ara h9, Ara h10, Ara h11, Ara h12, Ara h13, a peptide fragment thereof, or a combination thereof. In another aspect, the allergen is an allergen to a plant, pollen, animal, arthropod, insect, fungus, or venom. In another aspect, the allergen is an aeroallergen, pollen allergen, animal allergen, dust mite allergen, cockroach allergen, or mold or fungi allergen, Hymenoptera allergen, or combinations thereof. In another aspect, the allergen is an extract derived from the allergic source material, or purified from the extract, or synthesized chemically or biologically, and is whole allergen or a fragment thereof of the allergen. In another aspect, the allergen can be a mixture of two or more allergens in a ratio from 0.001:100 to 100:0.001. In another aspect, the amount of the allergen loaded into the cleaned pollen in an amount that is below the threshold that triggers an allergic response to the allergen. In another aspect, the allergen is in, on, about, or a film coated on the cleaned pollen or a combination thereof. In another aspect, the method further comprises adding one or more adjuvants in any size, shape, form or physical state introduced in, on, or about the cleaned pollen or a combination thereof that improve the immune response against the allergen. In another aspect, an opening in the cleaned pollen is partially or fully closed with a biodegradable polymer. In another aspect, the cleaned pollen are ragweed pollen. In another aspect, the allergen amount is less than about 1 gram, more preferably less than about 100 mg, more preferably less than about 1 mg, more preferably less than about 500 microgram, and more preferably less than about 100 microgram. In another aspect, the allergen is a peanut allergen and the amount of the peanut allergen is between 1 nanogram to 1 gram per dose. In another aspect, the dosage of pollen is about 1 grams of pollen per dose, more preferably about 500 mg per dose, more preferably about 100 mg per dose, more preferably about 10 mg per dose, or more preferably less than 10 mg per dose. In another aspect, the composition has improved organoleptic properties when compared to allergen alone. In another aspect, a desensitization to the allergen in a subject treated with the composition is by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, about 70%, about 75%, at least about 80%, at least about 85%, or at least about 90% as compared to the subject prior to commencing the treatment, a subject receiving a placebo or a subject not receiving the treatment. In another aspect, the subject is a human subject. In another aspect, the subject is less than 2 years old, about 2 years old to about 12 years old, about 3 years old to about 12 years old, about 4 years old to about 12 years old, about 4 years old to about 11 years old, about 4 years old to about 10 years old, about 2 years old to about 9 years old, or greater than about 12 years old. In another aspect, a sustained unresponsiveness lasts for about 1 month, about 2 months, about 3 months, about 4 months, about 5 months, about 6 months, about 7 months, about 8 months, about 9 months, about 10 months, about 11 months, about 12 months, or greater than about 12 months after therapy has ended. In another aspect, a sustained unresponsiveness lasts for at least about 1 month, at least about 2 months, at least about 3 months, at least about 4 months, at least about 5 months, at least about 6 months, at least about 7 months, at least about 8 months, at least about 9 months, at least about 10 months, at least about 11 months or at least about 12 months after therapy has ended.

In yet another embodiment, the present invention includes a method for oral delivery of a therapeutic agent for reducing, desensitizing, or preventing an allergic reaction to an allergen, comprising: identifying a subject in need of preventing or reducing an allergic reaction to an allergen; cleaning a pollen to remove naturally-occurring allergic plant proteins to form a cleaned pollen; enclosing a therapeutically effective amount of an allergen in the cleaned pollen; and providing orally to a subject in need of immunotolerance with a therapeutically effective amount of an allergen in or on the pollen sufficient to induce immune tolerance to the allergen. In one aspect, the allergen is a food allergen. In another aspect, the allergen is an aeroallergen. In another aspect, the allergen is a plant, pollen, animal, arthropod, insect, fungus, or venom allergen. In another aspect, the allergen is an extract derived from the allergic source material, or purified from the extract, or synthesized chemically or biologically, and is whole allergen or a fragment thereof of the allergen. In another aspect, the allergen can be a mixture of two or more allergens in a ratio from 0.001:100 to 100:0.001. In another aspect, the allergen is a peanut or soy allergen. In another aspect, the immune response to the therapeutic agent is greater than or equivalent to oral immunotherapy with same allergen but without use of the cleaned pollen. In another aspect, the immune response is sustained for at least 7 months after treatment. In another aspect, the therapeutic agent has improved organoleptic properties when compared to allergen alone. In another aspect, the allergen is in, on, about, or a film coated on the cleaned pollen or a combination thereof. In another aspect, the method further comprises one or more adjuvants in any size, shape, form or physical state introduced in, on, or about the cleaned pollen or a combination thereof that improve the immune response against the allergen. In another aspect, the allergen is a food allergy allergen to a groundnut, peanut, milk, egg, tree nut, seed, fish, shellfish, crustacean, cereal, legume allergy, hazelnut, cashew, walnut, pecan, brazil nut, macadamia, chestnut, pistachio, coconut, almond, sesame, soy, kidney bean, black bean, common bean, chickpea, pea, cow pea, lentil or lupine allergy or a mustard seed allergy, or a combination thereof. In another aspect, the allergen is peanut allergy allergen that comprises Ara h1, Ara h2, Ara h3, Ara h4, Ara h5, Ara h6, Ara h7, Ara h8, Ara h9, Ara h10, Ara h11, Ara h12, Ara h13, a peptide fragment thereof, or a combination thereof. In another aspect, the allergen is an allergen to pollen, house dust mite, cockroach, mold, fungi, cat, dog, or bee venom, or a combination thereof. In another aspect, the allergen is an allergen to Der p 1, Der p 2, Der f 1, and Der f 2 for house dust mite; Bla g 2, Bla g 4, Bla g 5, and Per a 1 for cockroach; and Amb a 1 for ragweed. In another aspect, a desensitization to the allergen is by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, about 70%, about 75%, at least about 80%, at least about 85%, or at least about 90% as compared to the subject prior to commencing the treatment, a subject receiving a placebo or a subject not receiving the treatment. In another aspect, the subject is from about 2 years old to about 12 years old, about 3 years old to about 12 years old, about 4 years old to about 12 years old, about 4 years old to about 11 years old, about 4 years old to about 10 years old, or about 2 years old to about 9 years old, or greater than about 12 years old. In another aspect, a sustained unresponsiveness lasts for about 1 month, about 2 months, about 3 months, about 4 months, about 5 months, about 6 months, about 7 months, about 8 months, about 9 months, about 10 months, about 11 months, about 12 months, or greater than about 12 months after therapy has ended. In another aspect, the step of treating is carried out at a frequency, repetition, and duration that leads to desensitization to the allergen. In another aspect, the step of treating is selected from: at least once a day, at least more than once a day, about 10 times a day, about 30 times a day, about every other day, about every 3 days, about every 7 days, about every 14 days, about every 21 days, about every 30 days, about every 2 months, about every 3 months, about every 4 months, about every 6 months, about every 1 year, and each dose could be the same or it could be different, depending on the allergen.

BRIEF DESCRIPTION OF THE DRAWINGS

For a more complete understanding of the features and advantages of the present invention, reference is now made to the detailed description of the invention along with the accompanying figures and in which:

Figures 1A, 1B:
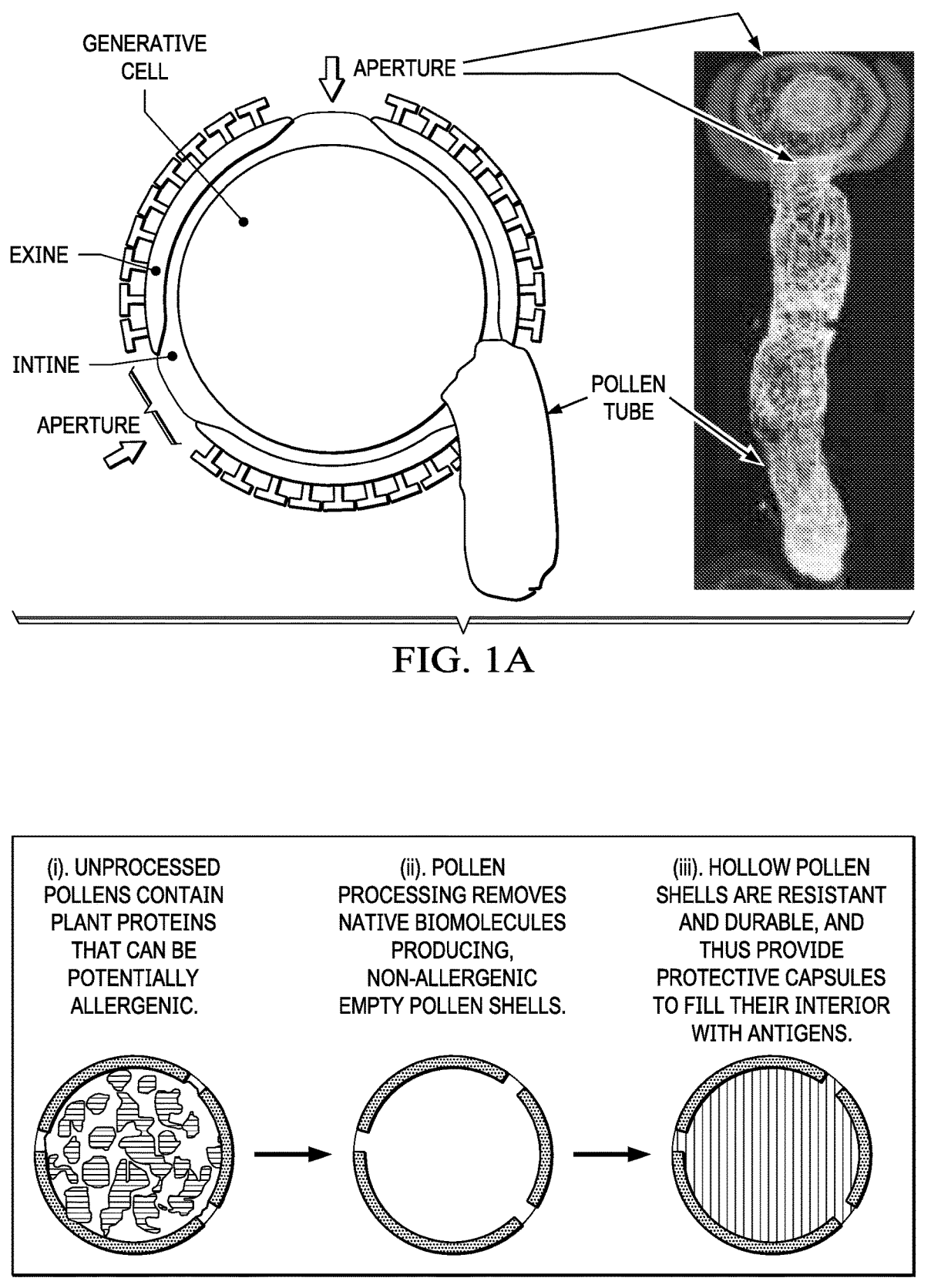

FIGS. 1A to 1E show pollens for oral delivery. (FIG. 1A) A pollen shell consists of an inner 'intine' and an outer 'exine' wall. At some locations, the exine is absent or softer to allow the pollen tube to emerge during fertilization. (FIG. 1B) Concept of chemically-cleaning pollens to remove allergic material naturally present in the pollens and to preferentially open their apertures, and using them to fill the clean pollen shell with molecules. (FIG. 1C, FIG. 1D) Scanning electron micrographs of raw (unclean) and chemically-cleaned ragweed pollen. Chemical cleaning opens the apertures but preserves the overall structure of pollens. (FIG. 1E) Confocal micrographs of chemically-cleaned ragweed pollen before and after filling them with fluorescently-labeled dextran (40 kDa). Pollens are naturally fluorescent under a broad range of excitation wavelengths and thus their shells auto-fluoresce.

(FIG. 3A) Oral vaccination schedule and dosage amounts. Mice were fed weekly doses by oral gavage for eight weeks. (FIG. 3B) Serum analysis at day 56 for anti-Ova IgG, IgG1, IgG2a and IgE response through ELISA.

(FIG. 4A) Schedule to create allergic mouse model, immunotherapy, and allergen challenge to test efficacy. (FIG. 4B) Elevated anti-Ova IgE in serum of mice after sensitization shows that the mice got successfully sensitized to Ova. (FIG. 4C). After challenge with allergen (Ova) the IgG and IgG1 levels of Ova+pollens group were similar to the Sc group, but IgG2a was higher in Ova+pollens oral delivery group. Notably, anti-Ova IgE in Ova+pollens was similar to Sc group. (FIG. 4D) Upper panel: Analysis of pro-inflammatory and anti-inflammatory cytokines in Bronchoalveolar lavage (BAL). Lower panel: Analysis of Th2 and Th1 cytokines in splenocyte culture supernatant through sandwich ELISA. mean±SEM. *p<0.05, p<0.01, *p<0.001, and ****p<0.0001. Note: Pollen used in formulation=ragweed pollen after cleaning.

(FIG. 5A) After allergen (Ova) challenge lung lavage was analyzed for different populations of immune cells. Flow cytometer was used to quantify percentage of neutrophils (Gr-1) (1), macrophages (CD11 b (M1/70) (2), mast cells (C-kit (CD117)) (3), B cells (CD 45-R (B220)) (4, 5), Th cells (CD4+) (6, 7), Tc cells (CD8+), and Tregs (CD4+CD25+) (8, 9). Cells associated with inflammatory response (neutrophils, macrophages, and mast cells) were low in Ova+pollens group compared to Ova alone, but similar to Sc group. All data illustrated as means±SEM. ****p<0.0001. (FIG. 5B) Lungs were harvested post allergen (Ova) challenge and fixed in formalin solution (4%, v/v) overnight. Tissues were sectioned and stained with periodic acid-Schiff (PAS) stain for analysis of mucus deposition inside the bronchiole wall (pink color). Bright field images of stained tissues show that Ova+pollen and Sc treatments significantly reduced mucus stimulation, while Ova alone and pollen alone did not. Arrows point to bright pinkish stain of PAS stain indicating presence of mucus. Note: Pollen used in formulation=ragweed pollen after cleaning.

(FIG. 6A) Schedule to vaccinate mice, create allergic sensitization against Ova, and perform allergen challenge to check efficacy. (FIG. 6B) After vaccination, the group vaccinated with Ova+pollen successfully induced Ova-specific IgG, IgG1, and IgG2a in mice. IgG and IgG1 from Ova+pollen vaccination was lower than the Sc route of vaccination, however, the IgG2a was higher in Ova+pollen group. Anti-Ova IgE levels were similar in Ova+pollen and Sc groups. (FIG. 6C). Ova-specific IgG, IgG1, and Ig2a antibodies after sensitization of the vaccinated mice were similar between Ova+pollen and Sc groups. (FIG. 6D) Ova-specific IgG, IgG1, and Ig2a antibodies after challenge of the sensitized mice were similar between Ova+pollen and Sc groups. Notably, anti-Ova IgE in Ova+pollens and Sc groups was also similar.

(FIG. 7A) Analysis of pro-inflammatory and anti-inflammatory cytokines in Bronchoalveolar lavage (BAL) shows no significant difference between Ova+pollen and Sc groups. (FIG. 7B) Analysis of Th2 and Th1 cytokines in splenocyte culture supernatant through sandwich ELISA. Ova+pollen group had higher Th1 cytokines over Sc group. mean±SEM. $*p<0.05$, $p<0.01$, $*p<0.001$, and $****p<0.0001$. Note: Pollen used in formulation=ragweed pollen after cleaning.

(FIG. 8A) After allergen (Ova) challenge lung lavage was analyzed for different populations of immune cells. Flow cytometer was used to quantify percentage of neutrophils (Gr-1) (1), macrophages (CD11b (M1/70) (2), mast cells (C-kit (CD117)) (3), B cells (CD 45-R (B220)) (4, 5), Th cells (CD4+) (6, 7), Tc cells (CD8+), and Tregs (CD4+CD25+) (8, 9). Cells associated with inflammatory response (neutrophils, macrophages, and mast cells) were low in Ova+pollens group compared to Ova alone, but similar to Sc group. All data illustrated as means±SEM. $****p<0.0001$. (FIG. 8B) Lungs were harvested post allergen (Ova) challenge and fixed in formalin solution (4%, v/v) overnight. Tissues were sectioned and stained with periodic acid-Schiff (PAS) stain for analysis of mucus deposition inside the bronchiole wall (pink color). Bright field images of stained tissues show that Ova+pollen and Sc treatments significantly reduced mucus stimulation, while Ova alone and pollen alone did not. Arrows point to bright pinkish stain of PAS stain indicating presence of mucus. Note: Pollen used in formulation=ragweed pollen after cleaning.

(FIG. 9A) Vaccination schedule. (FIG. 9B) Anti-PE IgG, IgG1, IgG2a and IgE responses in serum collected on day 56. Pollens help to generate a strong immune response as compared to PE only.

(FIG. 10A) Schedule and doses for sensitization and oral peanut challenge in Balb/c mice with peanut extract (PE). (FIG. 10B) Measurement of anaphylaxis indicators after oral challenge of mice with PE. (i) Drop in body temperature measured with rectal probe, (ii) Anaphylactic score: A scoring system based on mouse activity was used to evaluate anaphylactic severity (10, 11); 0: No symptoms; 1: Hypersensitivity to touch, irritation/aggression; 2: Puffiness around the eyes, pilar erection, reduced activity with increase respiratory rate; 3: Cyanosis around the mouth and tail, labored breathing, lying flat; 4: Loss of consciousness, no activity upon prodding, tremor or convulsions; 5: Death, (iii) PE-specific IgE antibodies, and (iv) histamine concentration in plasma. All data illustrated as mean±SEM. $*p<0.05$, $p<0.01$, $*p<0.001$, and $****p<0.0001$.

(FIG. 8A) Schematic of the experiment. (FIG. 11B) Transepithelial electrical resistance measurement after addition of ragweed for 24 h or EDTA from 23rd to 24th hour. (FIG. 11C) Cytotoxicity of pollen. Caco-2 cells were cultured with different concentrations of pollen or poly(lactic-co-glycolic) acid (PLGA) particles for 6 h. Cell membrane damage was assessed by Lactate Dehydrogenase (LDH) assay. (FIG. 11D) Cytokine secretion by Caco-2 cells. Caco-2 cells were cultured with 2 mg/ml of pollens for 24 h. IL-6, IL-8, and MCP-1 cytokines released from cells were measured by ELISA. Values shown are means±SD for three independent experiments. $p \leq 0.001$ [*], $P \leq 0.0001$ [**]. ns=not significant.

(FIG. 12A-FIG. 12B) Phagocytosis of ragweed pollen by mouse macrophage cells. Pseudo colored scanning electron micrographs of ragweed pollen phagocytosed by macrophage cells (J774A.1). (FIG. 12C) Bone marrow macrophages (BMMs) and (FIG. 12D) Bone marrow dendritic cells (BMDCs) were cultured with 500 μg/ml of ragweed pollens for 24 h, and the cytokines released from cells were measured by ELISA. LPS was used as a positive control and untreated cells were used as a negative control. LPS treated positive controls were excluded from statistical analysis. Values shown are means±SD for three independent experiments. $p \leq 0.01$ [], $p \leq 0.001$ [*], $p \leq 0.0001$ [****]. nd=not detectable. (FIG. 12E) Cell surface expression of activation and maturation markers in BMDCs. Cells were cultured for 48 h in presence of RW (100 μg/ml) or LPS (50 ng/ml). Cell surface expressions were analyzed using flow cytometer after staining with the appropriate antibody.

(FIG. 13A) Peanut protein extract (PE) was incubated with ragweed pollens. SEMs of the pollen surface before and after incubation, and after washing are shown. SDS PAGE of clean pollen (before) incubation, and after incubation and washing are shown. (FIG. 13B) Mice were fed ragweed (5 mg) and 24 h later they were euthanized. Confocal micrographs of intestinal segments show ragweed pollen in the intestinal wall. Ragweed pollens are autofluorescent in a broad range of excitation.

DETAILED DESCRIPTION OF THE INVENTION

Figure 1C:
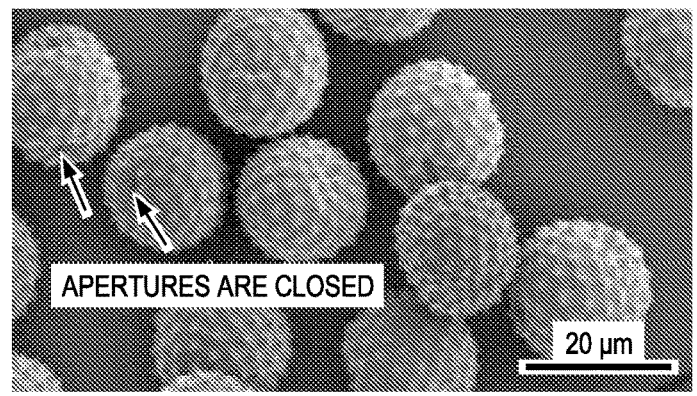
Figure 1D:
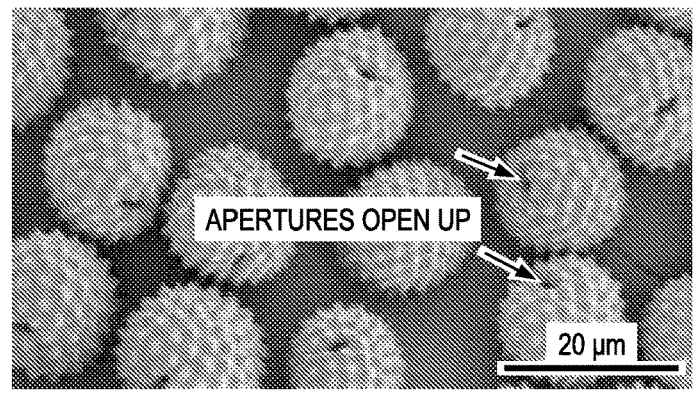
Figure 1E:
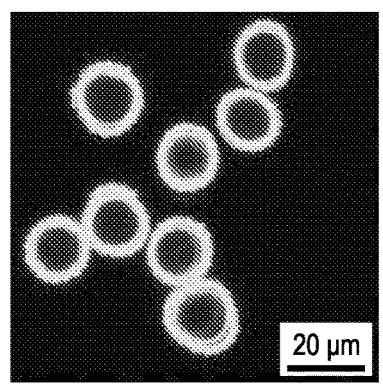
Figure 1E:
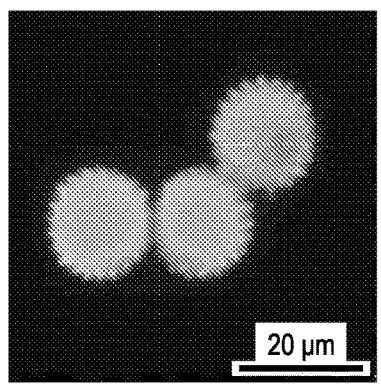
Figure 2G:
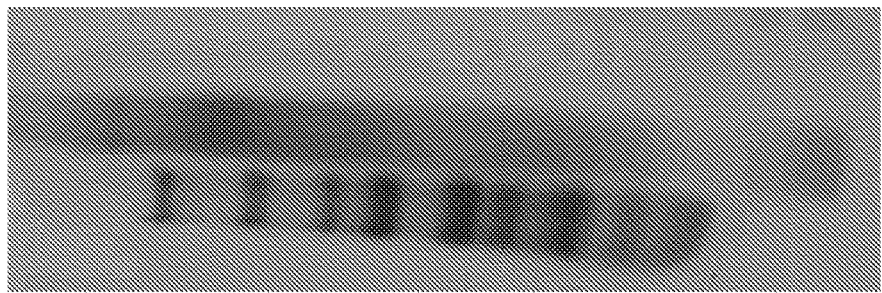
FIGS. 2A to 2G show Ragweed pollen before and after chemical treatment, which is a process to clean pollens for removal of allergic material. Ragweed pollens are not damaged after chemical treatment as can be seen by comparing SEMs of pollens before (FIG. 2A, FIG. 2C) and after (FIG. 2B, FIG. 2D) treatment. If pollens are manually cracked and then imaged, one can see natural biomolecules in the raw/unclean pollen (FIG. 2E), which are completely removed after treatment (FIG. 2F). The inventors also treated raw and cleaned pollen with SDS buffer and heated them to 95° C. for 10 min to extract any small amount of protein and ran the solution on a gel (FIG. 2G). It can be seen that as expected raw pollens have proteins, but treated and clean pollens do not have detectable proteins.
Figure 2B:
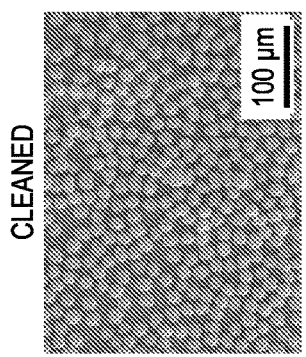
Figure 2D:
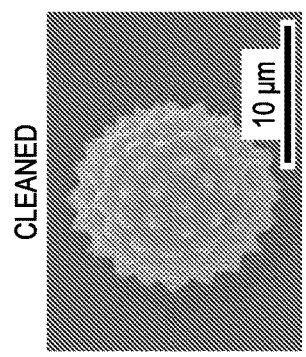
Figure 2F:
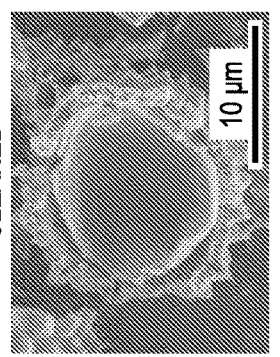
Figure 2A:
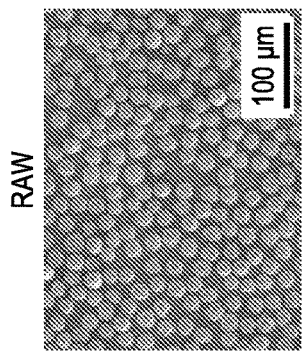
Figure 2C:
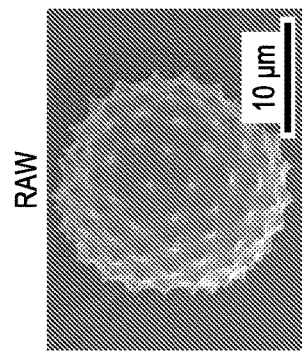
Figure 2E:
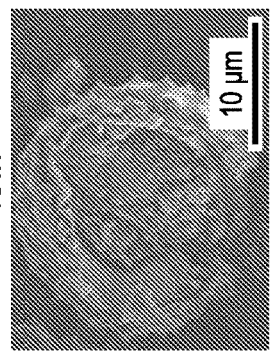

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

As used herein, the term "desensitization" refers to increasing the patient's threshold to allergen reactivity (i.e., the amount of allergen that can be safely tolerated by the patient). To maintain 'desensitization' the patient has to continue ingesting the food allergen at a 'maintenance dose' at regular intervals. In the case of respiratory or venom allergen the desensitization is thought to be achieved after maintenance phase shots, and this phase typically lasts many years.

As used herein, the phrase "sustained unresponsiveness" refers to the ability of the patient to be non-responsive to food allergen ingestion after completion of OIT without the need to be on a 'maintenance dose', and it is considered the desirable treatment endpoint.

As used herein, the term "subject" is used to mean an animal, for example a mammal, including a human or non-human. The terms subject and patient can be used interchangeably. The subject can be a child or an adult of any age. In one embodiment, a subject is from about 2 to about 30 years old. In a further embodiment, the subject is human. In another embodiment, the subject is human and is from about 2 years old to about 12 years old. In a further embodiment, the subject is a human subject and is from about 4 years old to about 11 years old or about 4 years old to about 10 years old.

As used herein, the term "treating" or "treatment" refers to the ability to achieve desensitization to the respective allergen, and/or long-term unresponsiveness (also referred to as sustained unresponsiveness). In one embodiment, the desensitization is characterized relative to the same subject, prior to commencing therapy, or compared to a subject receiving placebo or not receiving treatment. In one embodiment, the subject is desensitized by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, about 70%, about 75%, at least about 80%, at least about 85%, or at least about 90% as compared to the subject prior to commencing therapy, a subject receiving a placebo or a subject not receiving treatment.

An "effective amount" of an allergen is an amount of allergen that can provide desensitization to the allergen, and/or the increase in eliciting dose of the allergen. The effective amount can be delivered in a single treatment step, or as part of a treatment regimen where multiple doses are given during the treatment regimen. The treatment regimen can include substantially the same dose for each allergen administration, or can comprise escalation of the allergen dose with or without escalation in dose of pollen. In one embodiment the dose is escalated at least one, at least two or at least three times.

Successful desensitization can be characterized in one embodiment, by a decrease in the number of allergen specific IgE antibodies, and/or increased production of T regulatory cells. The T-regulatory cells in one embodiment, are Tr1 cells (produce IL-10, IL-10+), (ii) Th3 cells (produce TGF-β, latency associated peptide:LAP+), (iii) CD4+CD25+forkhead box P3:Foxp3+Tregs, or a combination thereof.

In another embodiment, successful desensitization is characterized by an increase in cytokine production (e.g., IL-10, TGF-β), increased production of IgG allergen specific antibodies (e.g., IgG4 in humans, IgG2a in mice), decreased number of mast cells (e.g., at the site of allergen exposure (e.g., the gastrointestinal tract (GI) in the case of food allergens and the respiratory tract in the case of aero allergens) as compared to prior to treatment), decreased number of basophils (e.g., at the site of allergen exposure (e.g., the gastrointestinal tract (GI) in the case of food allergens and the respiratory tract in the case of aero allergens), or a combination of the foregoing.

Successful treatment can also be measured by an increase in the eliciting dose of the allergen, as compared to the eliciting dose prior to initiation of treatment. The "eliciting dose" of an allergen or allergenic food, as used herein, is the lowest dose of allergen or allergenic food containing the allergen, that causes a response in a subject that is sensitized to the allergen, e.g., symptoms of an allergic reaction. "Eliciting dose" can also be used interchangeably with "threshold dose". The symptoms can be skin inflammation/redness, upper airway (eyes, nose, and throat), lower airway (lungs), gastrointestinal, cardiovascular and/or neurological symptoms, as assessed by one of ordinary skill in the art. In one embodiment, the symptom is a mild, objective symptom in a sensitized subject, e.g., a highly sensitized subject (50).

Low dose challenges can begin, e.g., at 10 μg of the allergen and can continue to increase based on the judgement of one of ordinary skill in the art. In one embodiment, a 30 minute or 1 hr. interval is used between doses. In one embodiment, the dose increase is an increase in an order of magnitude.

In one embodiment, a peanut allergen challenge comprises the administration of a peanut flour to a subject. The peanut flour can be defatted, and can comprise Florunner, Virginia, or Spanish peanut flour, or a combination thereof. In one embodiment, the peanut flour comprises equal parts Florunner, Virginia and Spanish peanut flour. In another embodiment, roasted peanuts are used as the challenge material. The foregoing compositions can also be used with pollens provided herein.

"Long term unresponsiveness" and "sustained unresponsiveness" are used interchangeably herein, and refer to the lack of clinical reactivity to the exposed allergen (e.g.: ingested food allergen or seasonal exposure to pollen or exposure to cat or exposure to bee sting) for 1 month to 1 year or more after therapy has ended. In one embodiment, the sustained unresponsiveness lasts for about 1 month, about 2 months, about 3 months, about 4 months, about 5 months, about 6 months, about 7 months, about 8 months, about 9 months, about 10 months, about 11 months or about 12 months after therapy has ended. In one embodiment, the sustained unresponsiveness lasts for at least about 1 month, at least about 2 months, at least about 3 months, at least about 4 months, at least about 5 months, at least about 6 months, at least about 7 months, at least about 8 months, at least about 9 months, at least about 10 months, at least about 11 months or at least about 12 months after therapy has ended.

In one embodiment, the food allergy is a milk, fish, shellfish or nut allergy. In one embodiment, the food allergy is a nut allergy. In a further embodiment, the nut allergy is a soy or a peanut allergy. In even a further embodiment, the nut allergy is a food allergy.

The one or more pollens of same species or mixture of different species can be used to delivery one or more food or aero or venom allergens or a combination thereof to a subject in need thereof in order to desensitize the subject to the allergen, and/or to obtain a sustained unresponsiveness to the allergen.

The term "allergen" refers to an immunogenic molecule (or a combination thereof) involved in an allergic reaction contained in food or air or venom or other sources. The allergen exposure might occur via ingestion of food, respiratory route, skin contact, eye contact or contact at other parts of the body. The allergen in one embodiment, is a lipid, carbohydrate, protein, peptide, polypeptide, or a combination thereof. In one embodiment, the allergen is a native food preparation, a food extract, or a purified protein, polypeptide and/or peptide composition. The allergen may be in a natural state, or produced artificially (e.g., by recombinant and/or enzymatic techniques, and or de novo synthesis for instance). The allergen in one embodiment, is structurally altered or modified to improve its stability or immunogenicity. The allergen in on embodiment is in admixture with one or more other constituents, such as an adjuvant or a stabilizer to stabilize the formulation or allergen or both. The allergen may be a mixture of several molecules (e.g., an extract such as a peanut protein extract). The allergen may be present in combination with other allergens, or in combination with other molecules from the food that are not immunogenic.

The invention may be used with any food or food allergens such as, without limitation, groundnut, peanut, milk, egg, tree nuts and seeds (such as but not limited to: hazelnut, cashew, walnut, pecan, brazil nut, macadamia, chestnut, pistachio, coconut, almond, sesame, mustard), fish, shellfish, crustaceans, cereals (e.g., wheat, corn, oat, barley, rye, rice, sorghum, spelt), legumes (e.g., soy, kidney bean, black bean, common bean, chickpea, pea, cow pea, lentils, lupine), or mixtures thereof.

In one embodiment, the allergen is a peanut allergen or a combination of peanut allergens. The peanut allergen in one embodiment is in the form of a peanut protein extract. Thirteen peanut allergens (Ara h1 through Ara h13) have been recognized by the Allergen Nomenclature Sub-Committee of the International Union of Immunological Societies (Zhou (51)). In one embodiment, the peanut allergen comprises one or more of Ara h1, Ara h2, Ara h3, Ara h4, Ara h5, Ara h6, Ara h7, Ara h8, Ara h9, Ara h10, Ara h11, Ara h12 or Ara h13, or a peptide fragment of one of the foregoing, or a combination thereof. In a further embodiment, the peanut allergen comprises Ara h1, Ara h2, Ara h3, a peptide fragment thereof, or a combination thereof. In yet another embodiment, the peanut allergen comprises Ara h1, a peptide fragment thereof, or multiple peptide fragments thereof.

Peanut Flour (PF) for use as an allergen composition can be obtained commercially, for example, from the Golden Peanut Company (Alpharetta, Ga.). The PF can be defatted, and can comprise in one embodiment, Florunner, Virginia, or Spanish PF, or a combination thereof. In one embodiment, the peanut flour comprises equal parts Florunner, Virginia and Spanish PF. In another embodiment, roasted peanuts are used as a source of allergen for the allergen composition. Peanut extract for use as an allergen composition in another embodiment, can be obtained commercially, for example, from Greer Labs (Lenoir, N.C.).

In one embodiment, the peanut allergen comprises Ara h1 (or a peptide fragment thereof), Ara h2 (or a peptide fragment thereof), and Ara h6 (or a peptide fragment thereof).

Figure 3A:
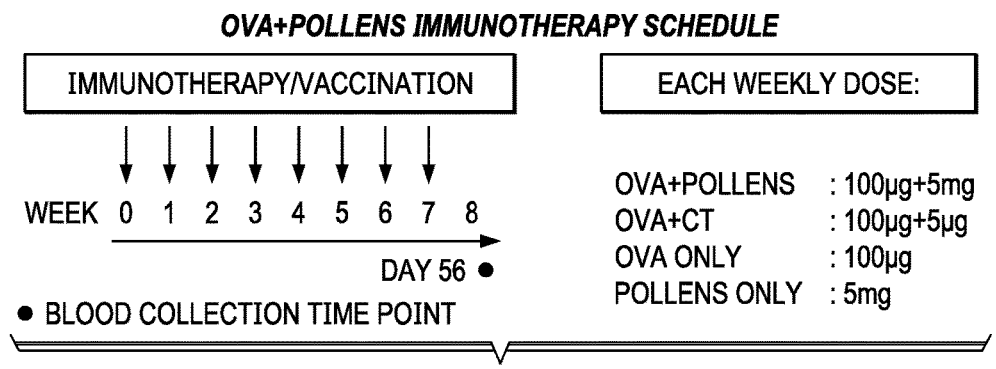
FIGS. 3A and 3B show Ragweed pollen upon addition to Ovalbumin (Ova) significantly enhance specific antibodies.
Figure 3B:
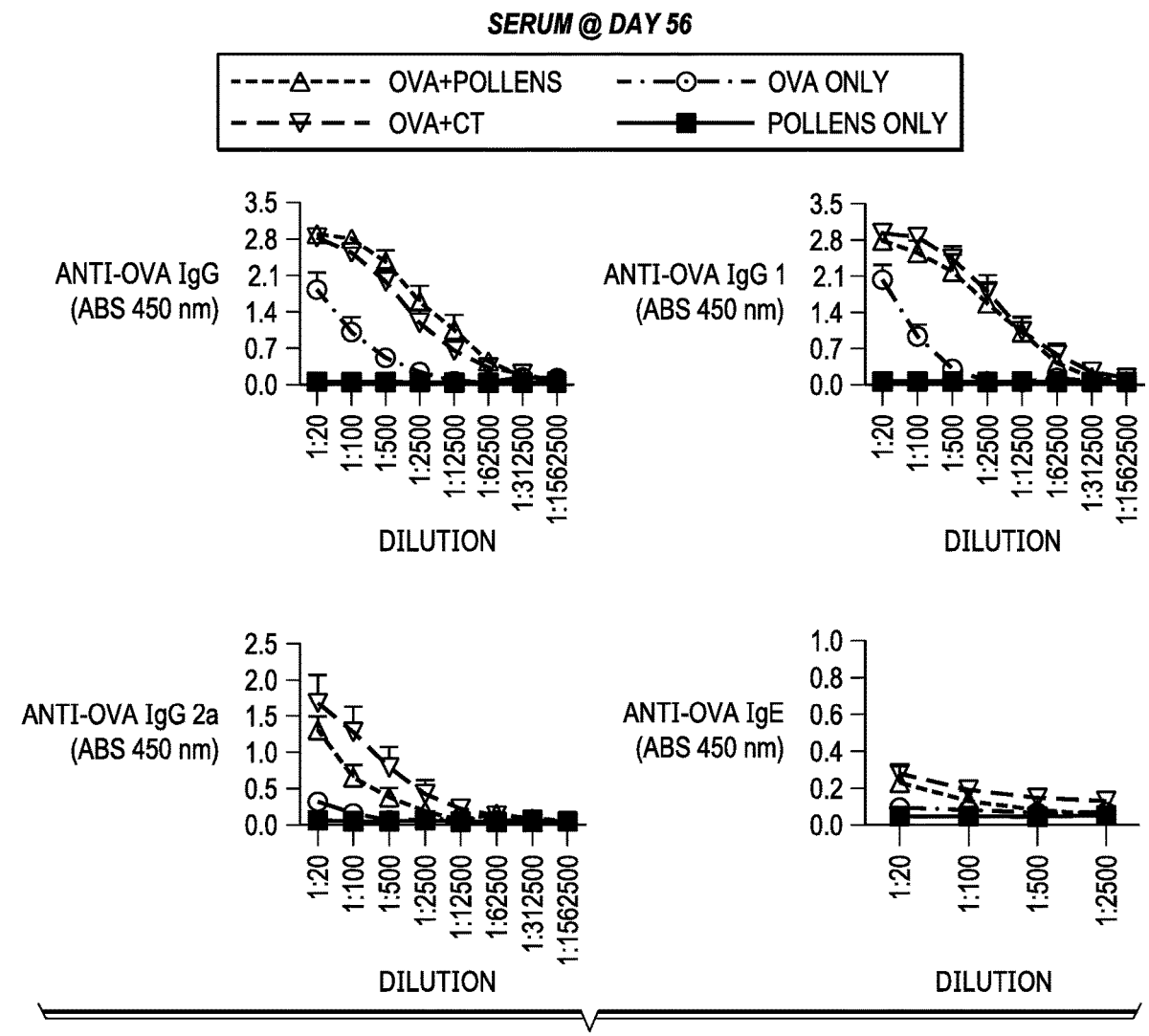
Figure 9A:
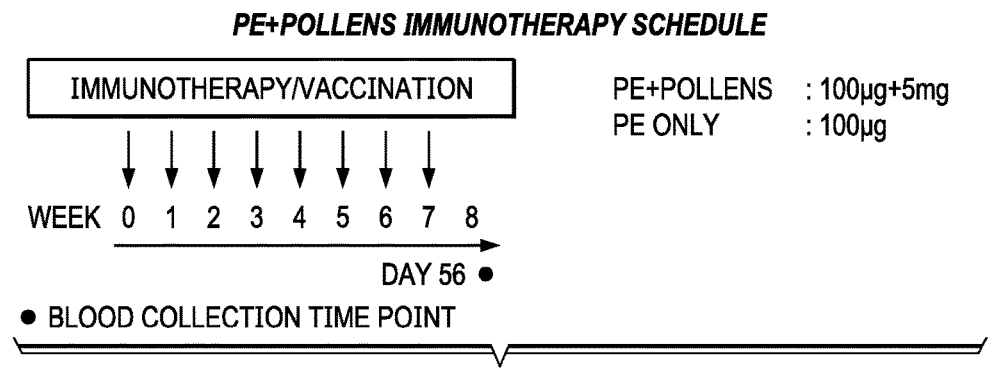
FIGS. 9A and 9B show pollens when added to peanut extract (PE) and fed orally to mice generate a strong antibody response over PE alone.
Figure 9B:
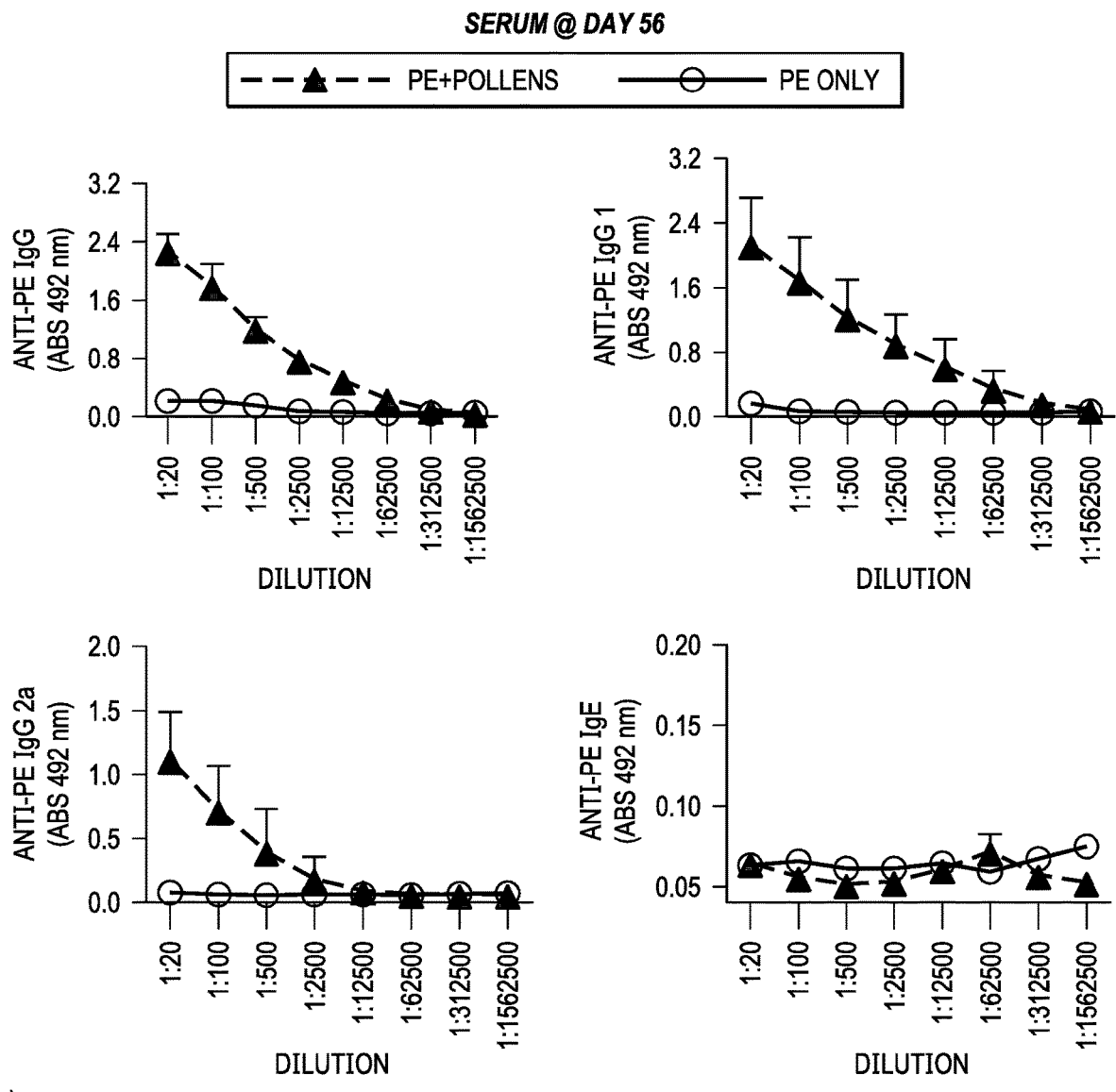
Figure 11A:
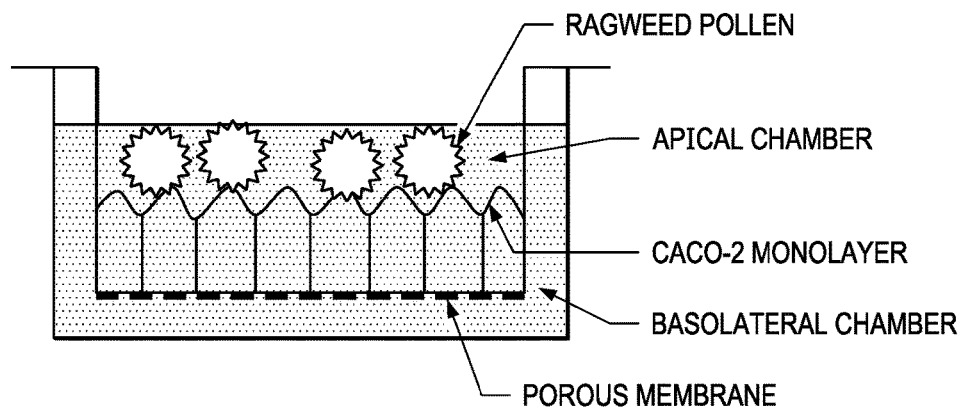
FIGS. 11A to 11D show the interaction of Caco-2 cells with ragweed pollen.
Figure 11B:
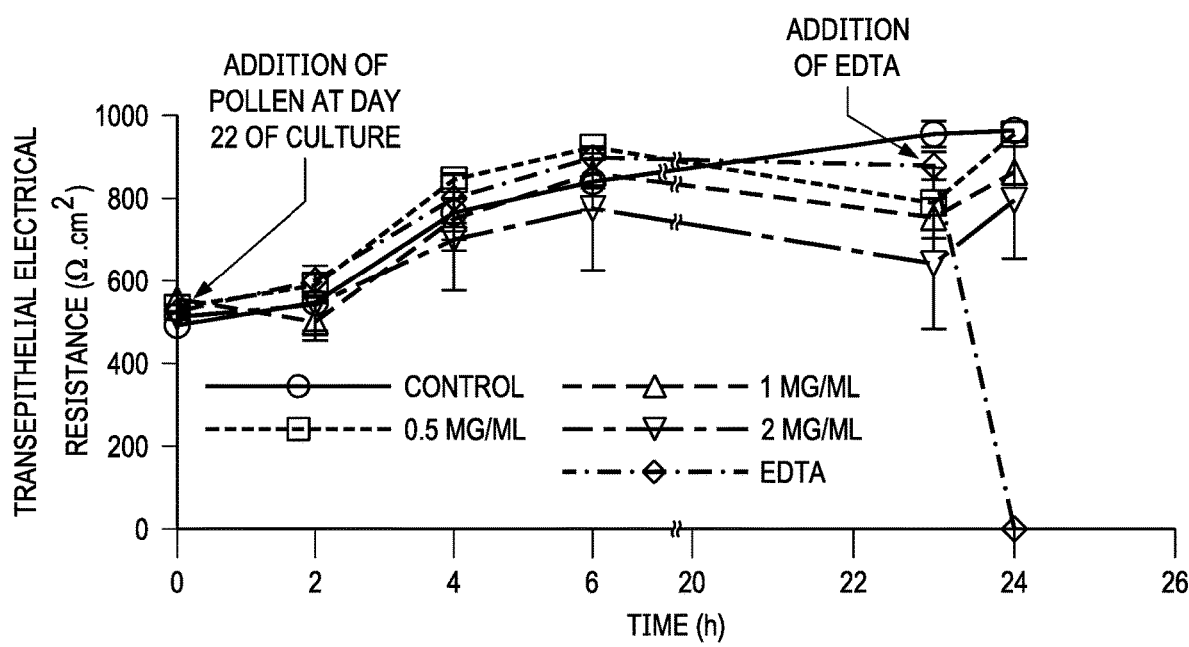
Figure 11C:
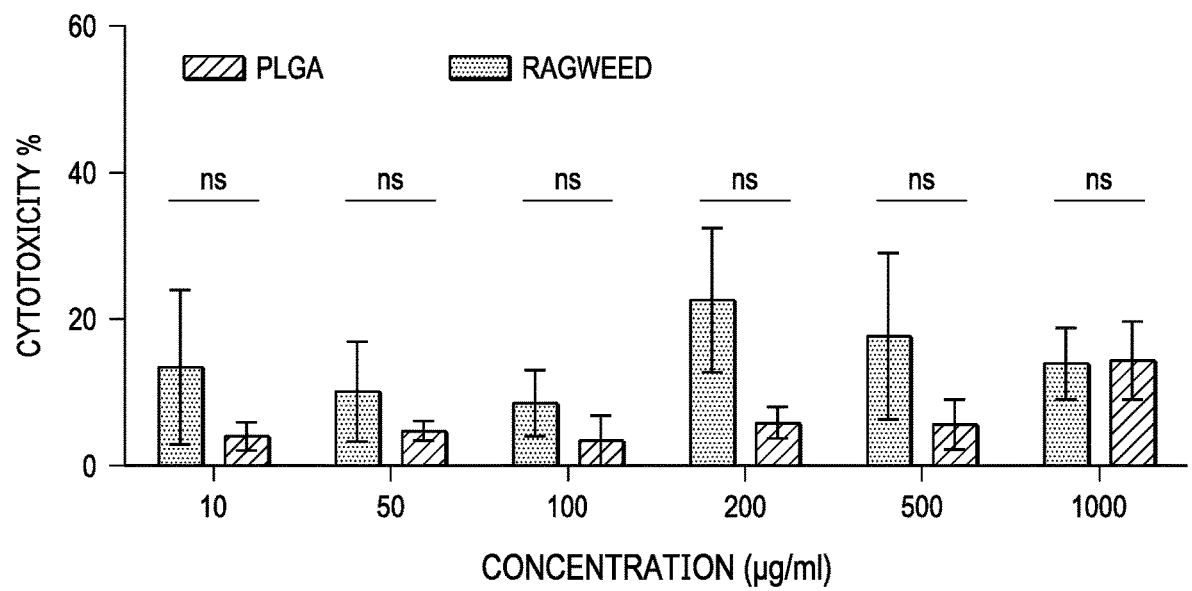
Figure 11D:
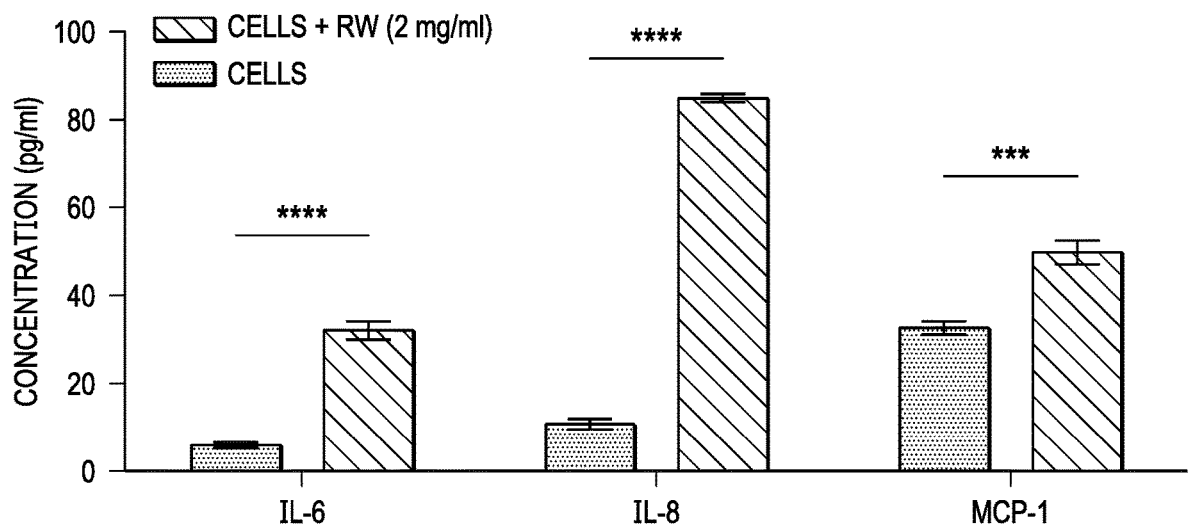
Figure 12A:
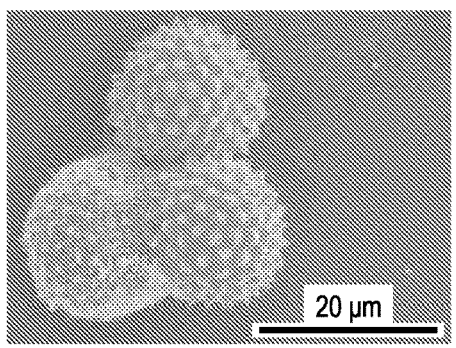
FIGS. 12A to 12E show the interaction of ragweed pollen with macrophages and dendritic cells.
Figure 12B:
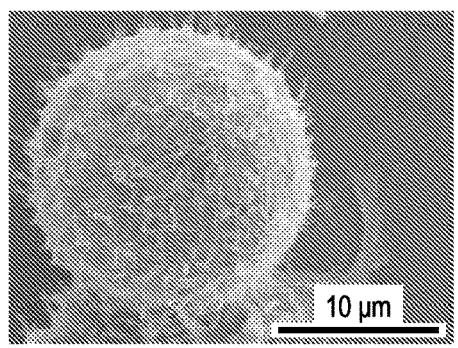
Figure 13A:
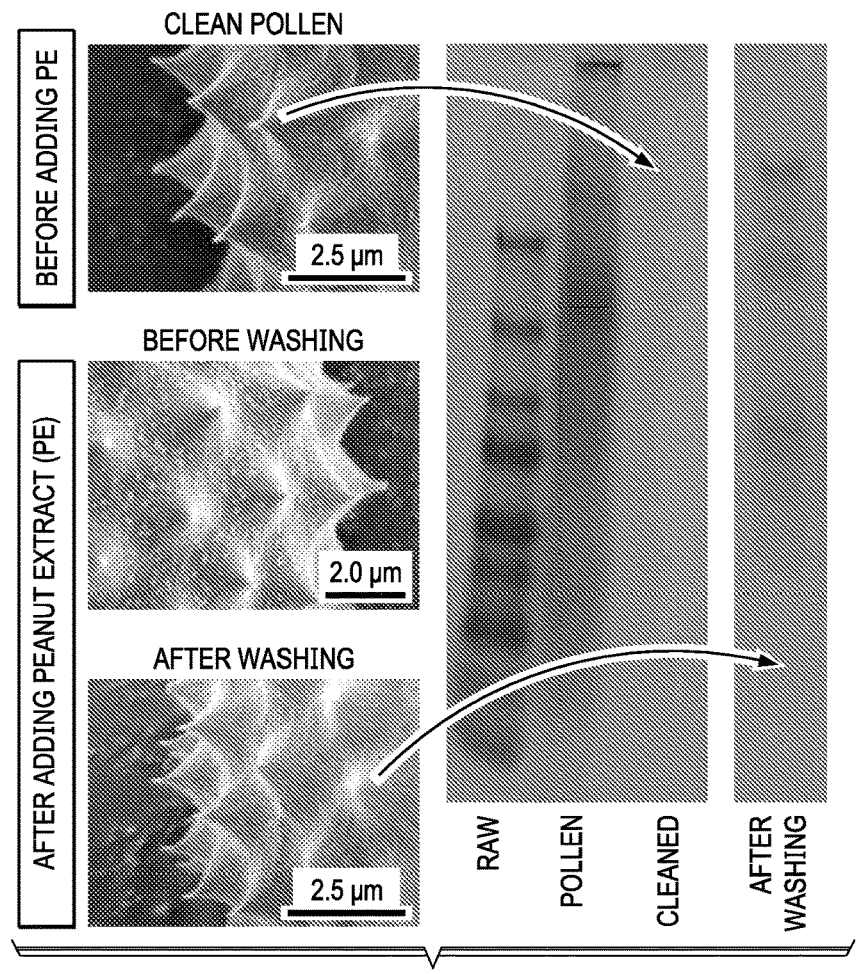
FIGS. 13A and 13B show.
Figure 13B:
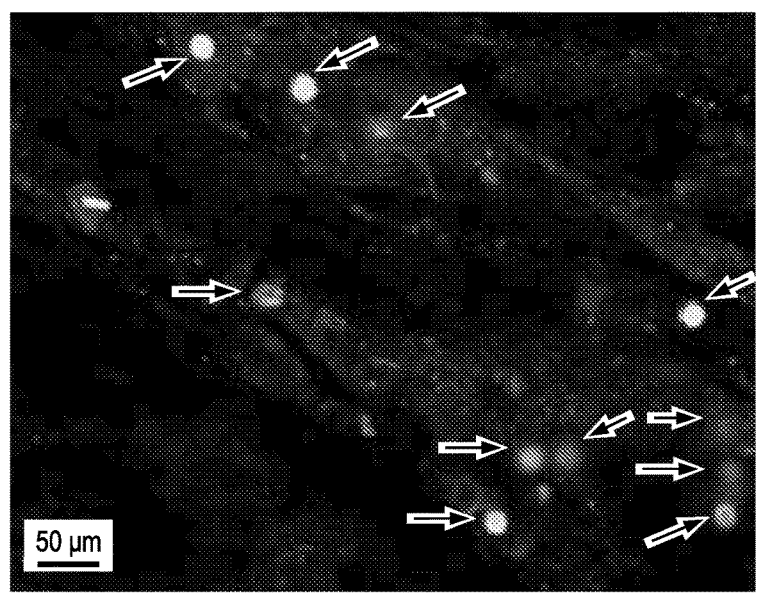

Representative linear epitopes for peanut allergens are provided in Zhou (51). For example, for Ara h1, epitope sequences that can be incorporated into the peanut allergen include PGQFEDFF (epitope #7), YLQGFSRN (epitope #8), FNAEFNEIRR (epitope #9), QEERGQRR (epitope #10), DITNPINLRE (epitope #11), NNFGKLFEVK (epitope #12), GNLELV (epitope #13), RRYTARLKEG (epitope #14), ELHLLGFGIN (epitope #15), HRIFLAGDKD (epitope #16), IDQIEKQAKD (epitope #17), KDLAFPGSGE (epitope #18), KESHFVSARP (epitope #19), NEGVIVKVSKEHVEELTKHAKSVSK (epitope #21), or a combination thereof.

Peptides that may be incorporated into an Ara h2 peanut allergen include HASARQQWEL (epitope #1), QWELQGDRRC (epitope #2), DRRCQSQLER (epitope #3), LRPCEQHLMQ (epitope #4), KIQR.DEDSYE (epitope #5), YERDPYSPSQ (epitope #6), SQDPYSPSPY (epitope #7), DRLQ..GRQQEQ (epitope #8), KRELRNLPQQ (epitope #9), QRCDLDVESG (epitope #10), or a combination thereof.

Peptides that may be incorporated into an Ara h3 allergen include IETWNPNNQEFECAG (epitope #1), GNIFSGFTPEFLAQA (epitope #2), VTVRGGLRILSPDRK (epitope #3), DEDEYEYDE--EDRRRG (epitope #4), or a combination thereof.

In one embodiment, the allergen is a legume allergen or a tree nut allergen. For example, the allergen in one embodiment is soy. In another embodiment, the allergen is almond, pecan, hazelnut, walnut or a combination thereof. It should be noted that certain patients are sensitized against more than one type of food allergen (1, 52), each of which is incorporated by reference herein in its entirety for all purposes). As such, some embodiments of the invention are directed to the delivery of multiple allergens to a patient in the treatment methods provided herein. Alternatively, an allergen is cross reactive to two different food substances, and therefore, in one embodiment, a cross reactive allergen can be used to desensitize a patient to multiple food allergens. In cross-reactivity, IgE antibodies against one allergen can bind to a different homologous allergen and trigger the adverse reaction similar to that elicited by its binding to the first allergen. Homologous allergens share structural similarity or common epitopes, which increases the chances of cross-reactivity. For example, peanut proteins share structural homology within the legume family (e.g. soy protein), and with certain tree nuts (e.g. almond, pecan, hazelnut, and walnut) (1, 53-55) each of which is incorporated by reference herein in its entirety for all purposes). Without limitation to food allergens, subjects are also often allergic to more than one aeroallergens or venoms. Therefore, in some embodiments the allergen can be a mixture of different food or aero or venom or combination thereof, and in same or different ratios. Cross-reactive allergens across different allergen groups (such as without limitation food, aero, or venom) can be used to desensitize subjects against multiple allergens.

Pollen grains are microscopic particles, whose sole purpose is to help in fertilization and sexual reproduction of the plant by safely delivering the male gamete (sperm cells) harbored in its interior to the female ovary in the flower (5). To execute its function, pollens have an extremely durable outer wall that is made of a tough biopolymer called sporopollenin. Sporopollenin is highly resistant to chemical degradation, and allows pollens to withstand tough climatic conditions such as extreme temperatures and drought conditions to protect the fragile male gamete cargo it carries (6-10).

Use of 'clean' pollen shells for oral allergen/antigen delivery. The present invention exploits the toughness and chemical durability of the pollen shells to deliver vaccines across the harsh environment of the stomach. The pollens are cleaned to remove allergy-causing plant proteins, followed by packaging of vaccine molecules in to the empty space inside the clean shell (FIGS. 1A to 1E) for transport across the harsh acidic and enzyme-rich environment of the stomach (11, 12). Upon arrival in the GI tract, pollens can extravasate across the epithelia through a process called persorption (11, 13), by which large particles with diameters of tens of micrometers can cross the gut epithelial barrier (14, 15). Attractive properties of pollen with ragweed as an example without limitation: (i) ragweed can persorb across mouse gut epithelia (FIG. 13B); (ii) stimulate the epithelial cells, macrophages, dendritic cells (DCs) in vitro to secrete pro-inflammatory cytokines (FIGS. 11D, 12B); (iii) can significantly enhance the antibody generation against orally delivered antigens/allergens even at low microgram doses (FIGS. 3B, 9B); (iv) the immune response is comparable to that induced by subcutaneous injection (a route typically used for airway allergy immunotherapy), and a positive control that uses cholera toxin (CT) as a potent but toxic oral adjuvant (FIGS. 4A-4D, 6A-6D); and (v) in an ovalbumin (ova) airway allergy model, oral delivery of 'ova+pollen' resulted in similar efficacy compared to subcutaneous route for 'treatment' of allergy (FIG. 4A-4D) or for 'prevention' of allergy (FIGS. 6A-6D); and lastly (vi) 'pollen+peanut extract' at just 100 µg peanut extract dose led to a significantly high serum IgG response (FIG. 9B) as compared to just 'peanut extract' oral delivery (which is used in current peanut oral immune-therapy (OIT)). Overall this shows the potential of pollen to be used to induce much higher immunomodulatory response when added to the allergen.

Pollen allergies are caused by pollen-specific proteins and biomolecules (16, 17) and not the pollen shell. One can readily relate to this fact by remembering that for skin allergy tests, it is the pollen extract that is applied on the patient's skin, and not the pollen shells. These proteins, lipids etc. naturally found in pollens are removed before the pollens are used in the teachings of this patent.

Figure 4A:
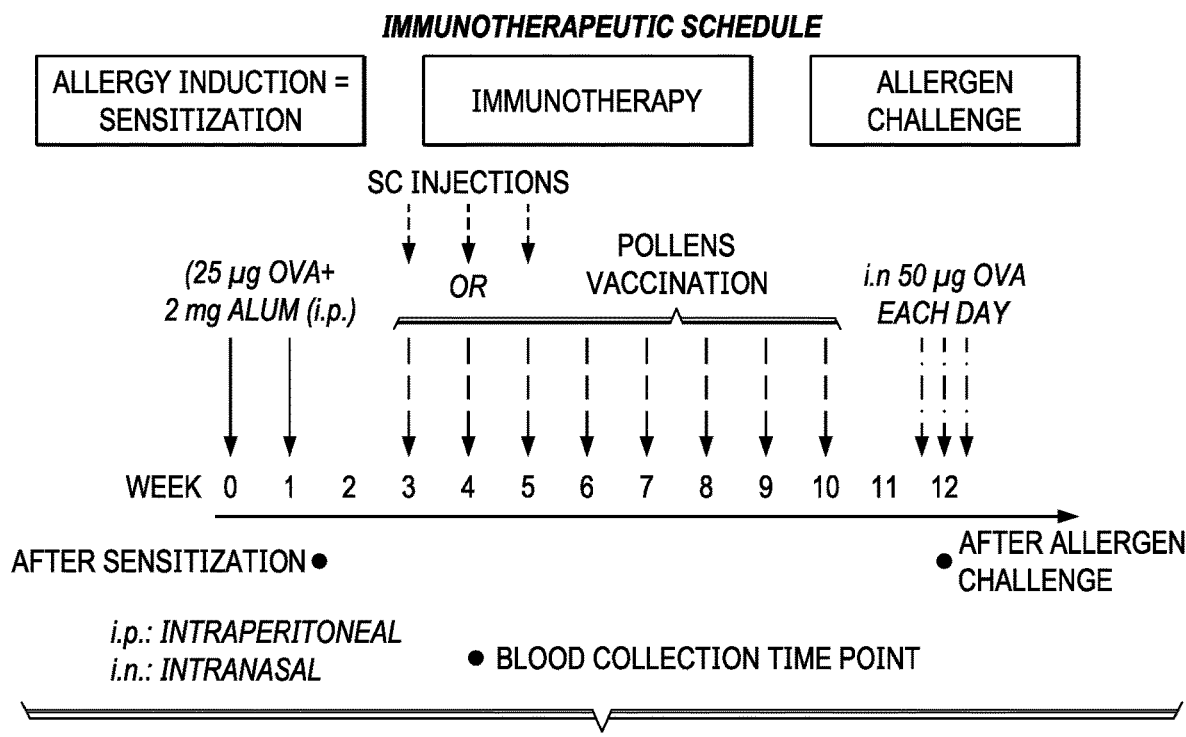
FIGS. 4A to 4D show Ova+pollen oral immunotherapy performs similar to subcutaneous (Sc) allergy shots in treating allergy in a mouse model of Ova-respiratory allergy.
Figure 4B:
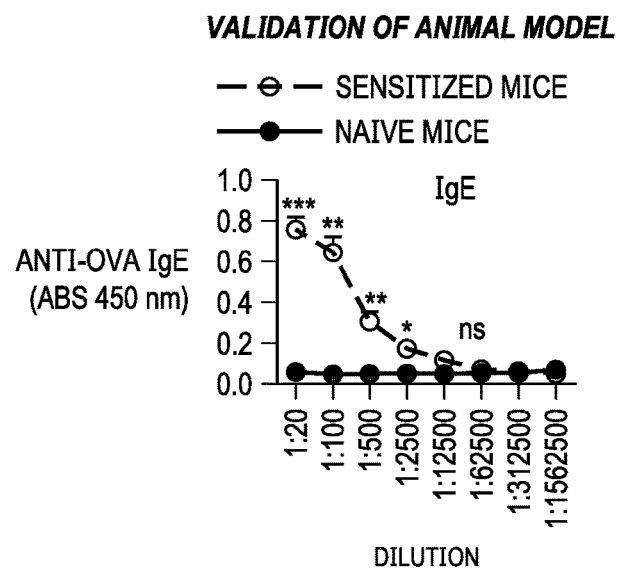
Figure 4C:
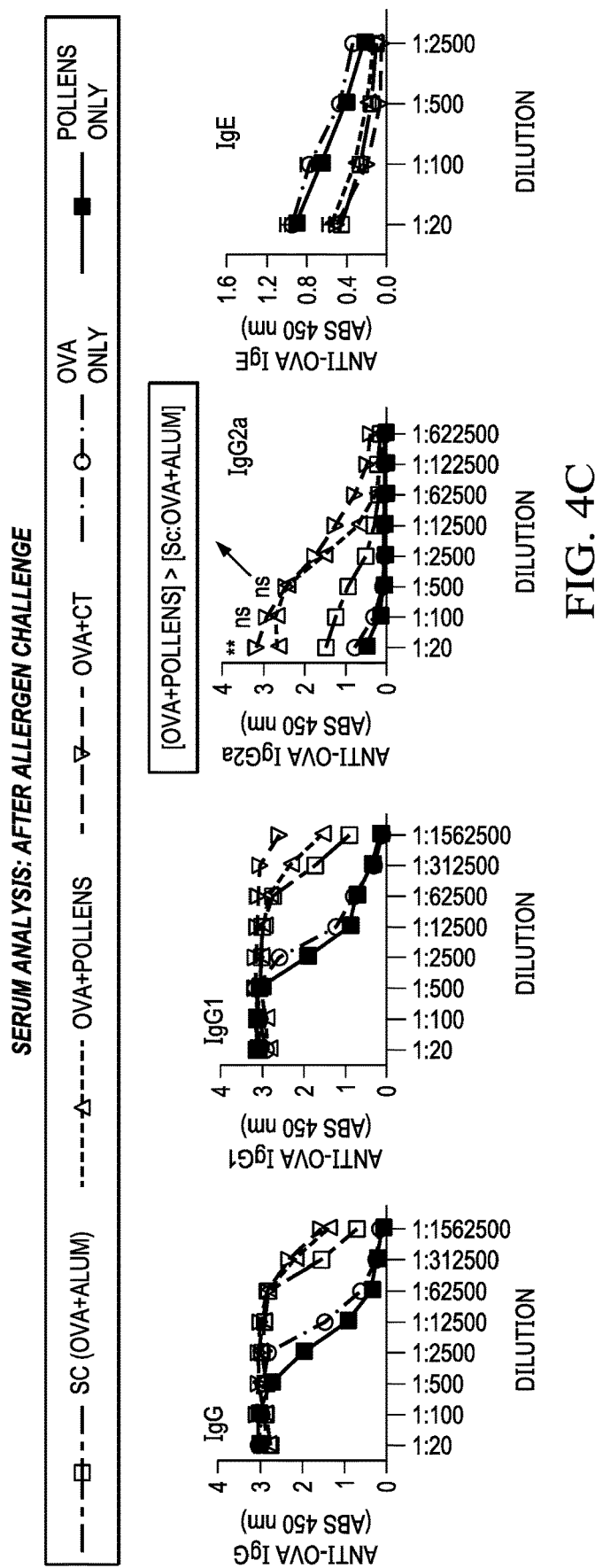
Figure 4D:
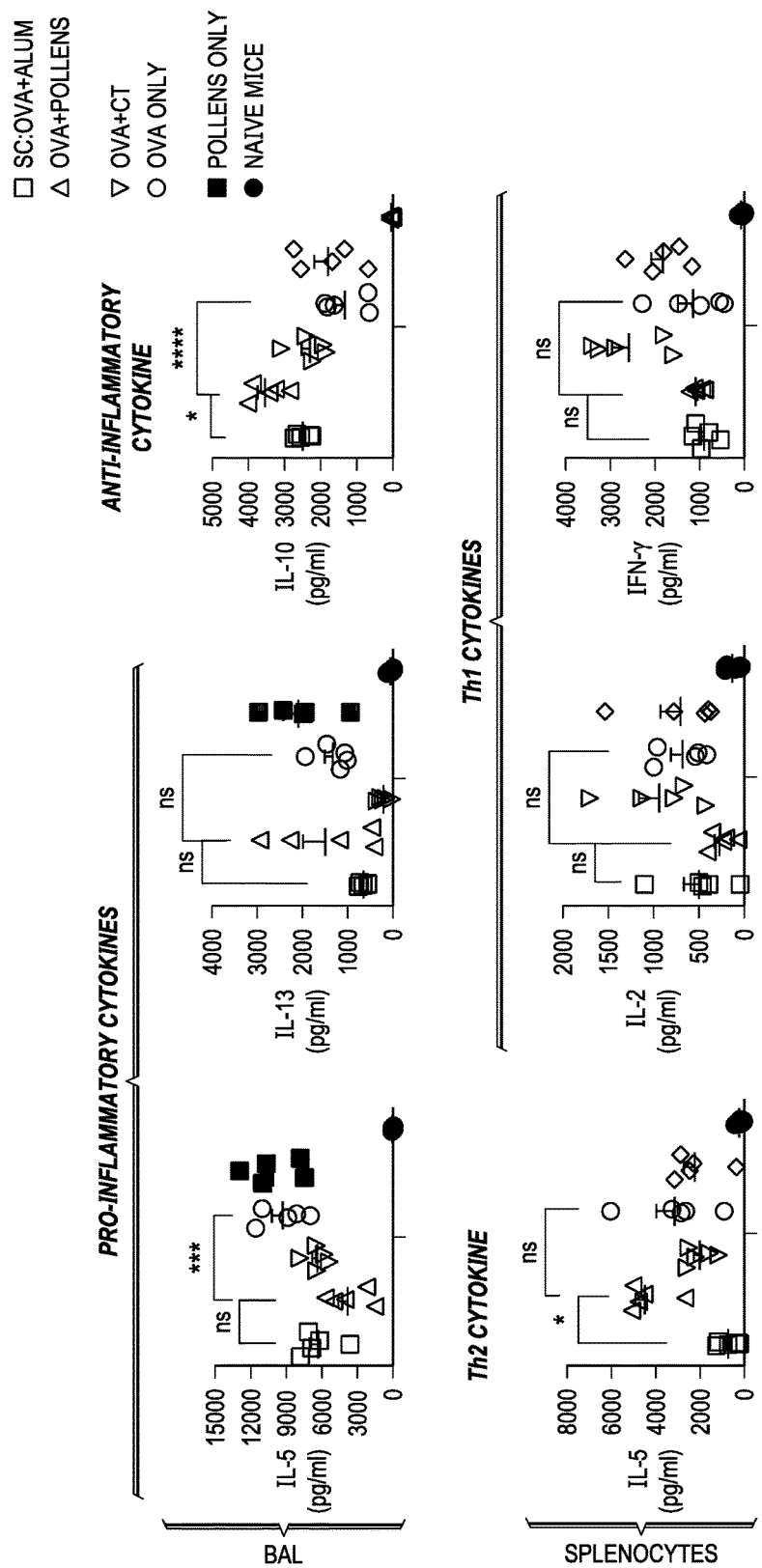

The present invention is provided with ragweed pollen as an example. The present invention uses clean ragweed pollens to enhance the immune response towards orally-delivered allergens (e.g.: Ova as a model aero allergen, and peanut as a food allergen). Pollens are themselves associated with airway allergies. Thus, the concept that they can actually be used to treat allergy is certainly new, counter-intuitive, and unexpected.

A major limitation of current oral immunotherapy protocols for food allergens is that the food allergen (such as peanut) oral dose is escalated to thousands of milligrams, which causes side effects. The present inventors have found that they do not need such high doses of the allergens. The inventors have found that upon addition of ragweed pollen, a small dose of just 100 μg of allergen (Ova or peanut extract) given weekly (not even daily as the current OIT protocols do) is successful in inducing a strong immune response (FIG. 3B and FIG. 9B). Thus, through this approach, the oral route is made safer.

Long-term effect. A major limitation of food allergen (such as peanut) OIT is that it offers short-term desensitization. This is in contrast to subcutaneous allergy shots used to treat environmental allergies (but not approved for food allergies), which can provide long-term desensitization. Pollen-based oral allergen vaccination can offer long-term desensitization as a result of sustained allergen-specific antibody levels.

Ragweed pollens remain intact and are devoid of native potentially-allergenic proteins after chemical treatment. Ragweed pollens were chemically treated via treatment with acetone (@60° C. for 12 h to remove lipids and other molecules soluble in organic solvent), phosphoric acid (@140° C. for 7 days to remove cellulosic components and proteins), and potassium hydroxide (@80° C. for 24 h to hydrolyze and remove proteins). Pollens were then thoroughly washed with water, acetone, and ethanol. After this extensive treatment, ragweed pollens are intact (compare before: FIG. 2A and FIG. 2C with after: FIG. 2B and FIG. 2D,), and the interior is completely cleaned (compare before: FIG. 2E with after: FIG. 2F). No proteins were detected in treated pollens when 5 mg ragweed (amount in one oral dose) were treated with SDS buffer (0.3 ml) at @95° C. for 10 min (FIG. 2G), while native proteins were seen in untreated ragweed exposed to SDS (FIG. 2G).

The preparation of pollen-based allergen formulation. Cleaned ragweed pollens are added to allergen (e.g. Ova) or allergen extract (e.g. peanut extract) and mild vacuum is applied to allow liquid to fill the ragweed pollens, and the dose is ready. This translates into an inexpensive process that can directly use the existing allergens or extracts already used for allergy testing. Ragweed pollen are also available in tons of quantity because pollen-collection is an existing well established industry since these pollens are required by pharmaceutical companies to make pollen extracts for allergy testing and treatment. Thus in fact, the waste of that process, i.e., ragweed pollen after allergen extraction, could form the raw material to produce chemically-treated clean pollens.

Ragweed oral immunotherapy efficacy for 'treatment' and 'prevention' of allergies has been demonstrated by the inventors in a conventional airway allergy mouse model where the subcutaneous allergy shot is available as a positive control for comparison. This control is not typically used in a food (such as peanut) allergy mouse model because it is not clinically relevant (NOTE: Peanut allergy is not treated with shots due to high risk (2, 3)).

Ragweed pollen increase ovalbumin (Ova)-specific immune response. To assess the efficacy of ragweed pollens for induction of allergen-specific immune response, Balb/c mice (n=5) were fed with Ova (100 μg)+ragweed-pollens (5 mg) weekly for eight weeks (FIG. 3A). As a positive control Ova (100 μg)+cholera toxin (CT) (5 μg) was used, and as negative controls Ova alone or pollens alone were used. After eight doses, mice were bled to check anti-Ova antibody response (FIG. 3B). Ova+pollens induced anti-Ova IgG and IgG1 response similar to Ova+CT but significantly higher than the Ova or pollens alone groups. Interestingly, Ova+pollens induced Ova-specific IgG2a equivalent to Ova+CT suggesting that ragweed pollens help activate the Th1 pathway. Further, the presence of low anti-Ova IgE in Ova+pollens group eliminates the possibility of allergy induction during oral ingestion of ragweed pollens, which is in agreement with previous reports on safe ragweed and other pollen ingestion by humans without complications (18-20).

Oral-immunotherapy with pollen+allergen can 'treat' airway allergy comparable to the subcutaneous allergy shot. To validate the therapeutic efficacy of Ova+pollen oral immunotherapy, first mice were made allergic (also known as sensitized) to Ova by intraperitoneal (i.p.) injection of Ova+alum mixture (25 μg Ova+2 mg alum) at week 0 and 1 (FIG. 4A). Successful generation of allergic mice was confirmed by high anti-Ova IgE serum levels (FIG. 4B). Post-sensitization, mice were treated with an oral dose of Ova+pollens weekly for eight weeks. As control groups, allergic (a.k.a. sensitized) mice were given (i) subcutaneous injection of Ova (25 μg)+alum (250 μg) to mimic the conventional subcutaneous allergen immunotherapy (Sc) weekly for three weeks, (ii) oral Ova (100 μg)+CT (5 μg) given weekly for eight weeks, (iii) Ova alone (100 μg) given weekly for eight weeks, and (iv) pollens alone (5 mg) given weekly for eight weeks. Sensitized mice without any treatment and naïve mice (no exposure to OVA at all) were also used as control groups. Allergen challenge: Two weeks post-immunotherapy, mice were challenged with a high dose of Ova (50 µg Ova per mouse per day) through i.n. route for three consecutive days. Anti-Ova IgG and IgG1 antibodies remained high for OVA+pollen group. Interestingly, anti-Ova IgG2a response was superior in Ova+pollens than the Sc group (FIG. 4C), again pointing to the activation of the Th1 pathway, which plays a significant role in suppression of airway inflammation (21) and food allergy (4). After euthanasia, in the bronchoalvelar lavage (BAL), low expression of pro-inflammatory cytokines IL-5 and IL-13 was seen in Ova+pollens group in contrast to Ova alone group (FIG. 4D), which further indicates the suppression in airway inflammation post-treatment. Interestingly, up-regulation of anti-inflammatory cytokine (IL-10) in Ova+pollen group indicates activation of T regulatory (Treg) cells. IL-10 cytokine is considered an anti-inflammatory cytokine expressed by T regulatory 1 (Treg1) cells, and it helps in suppression of airway inflammation (22), and regulates the expression of pro-inflammatory cytokines, and chemokines (23). Activation of Th1 pathway in Ova+pollen oral immunotherapy group was confirmed by high expression of Th1 cytokines in supernatant collected from splenocytes cultured in vitro under Ova re-stimulation. As seen in FIG. 4D (lower panel), the expression of IL-2 ($p=0.001$) and IFN-γ ($p<0.0001$) was significantly higher in Ova+pollens group than the Sc group, while the Th2 cytokine IL-5 was considerably lower in Ova+pollens than Ova alone.

Figure 5A:
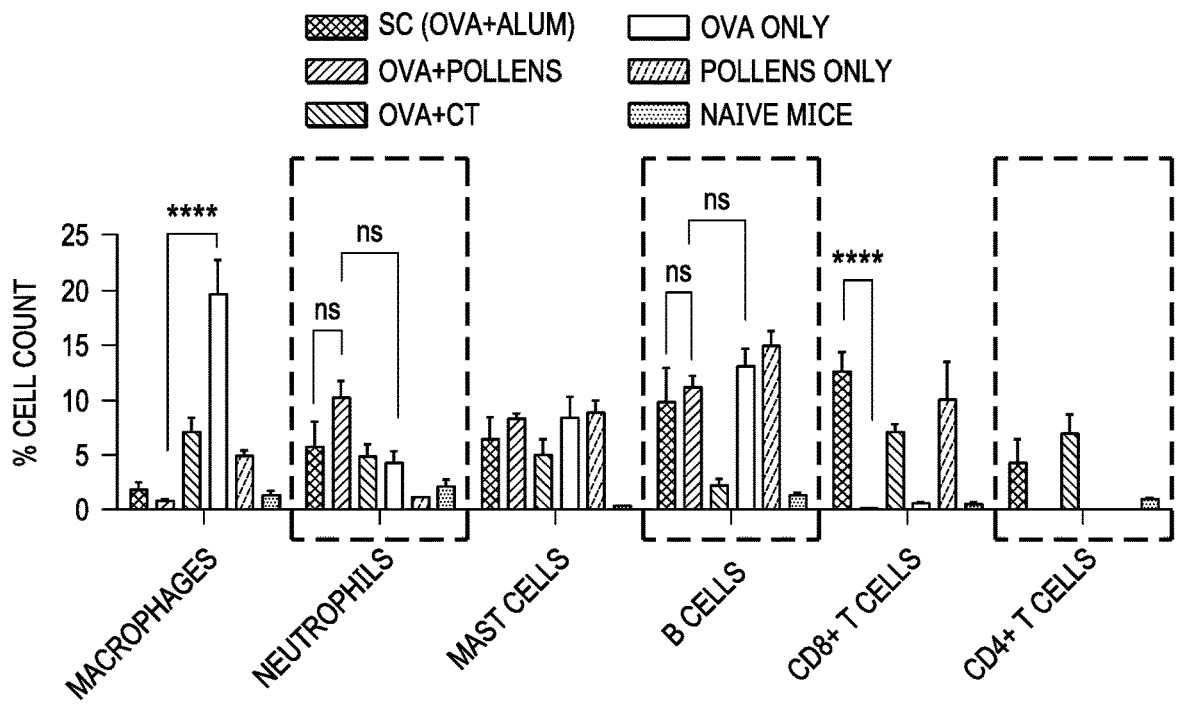
FIGS. 5A and 5B show Ova+pollen oral immunotherapy performs similar to Sc allergy shots in treating allergy in a mouse model of Ova-respiratory allergy.
Figure 5B:
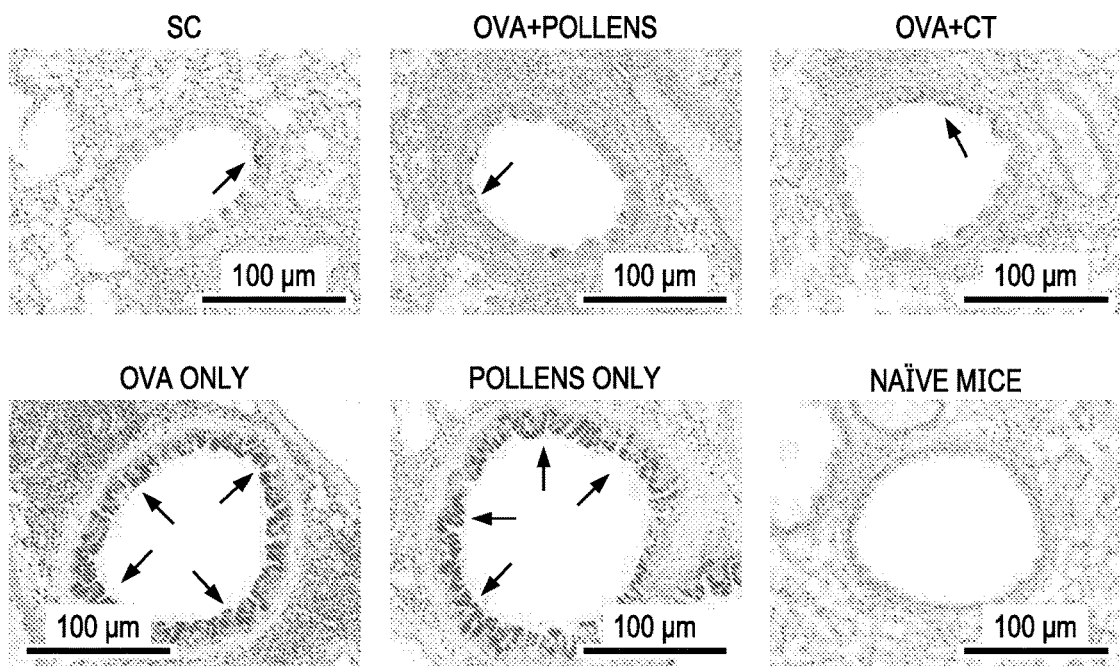

Oral allergy 'treatment' with Ova+pollen significantly suppresses allergic airway inflammation similar to subcutaneous shots. After euthanasia, in the BAL fluid infiltrating cell types were analyzed. Flow cytometry analysis (Attune NxT, Life Technologies, USA) showed a significantly ($p<0.05$) low percentage of neutrophil and macrophage cell counts in the Ova+pollens treated group as compared to Ova alone, but similar to Sc group (FIG. 5A). No considerable differences were observed in B, mast, CD4+ T cells and CD8+ T cells across all treatment groups. Further, lung tissues were fixed in formaldehyde, sectioned and stained with periodic-acid-Schiff (PAS) for mucus production. FIG. 5B shows that mucus production in Ova+pollens was negligible like the Sc group, but Ova alone group showed higher mucus production indicative of an inflammatory response.

Figure 6A:
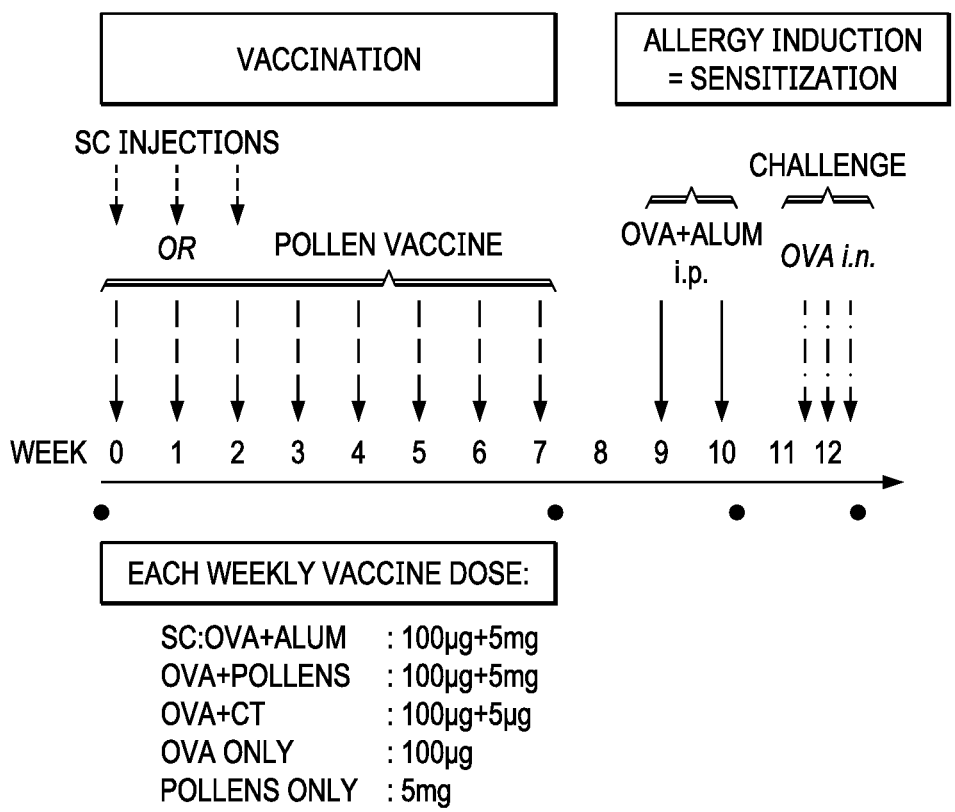
FIGS. 6A to 6D show Ova+pollen oral immunotherapy performs similar to subcutaneous (Sc) allergy shots in preventing allergy in a mouse model of Ova-respiratory allergy.
Figure 6B:
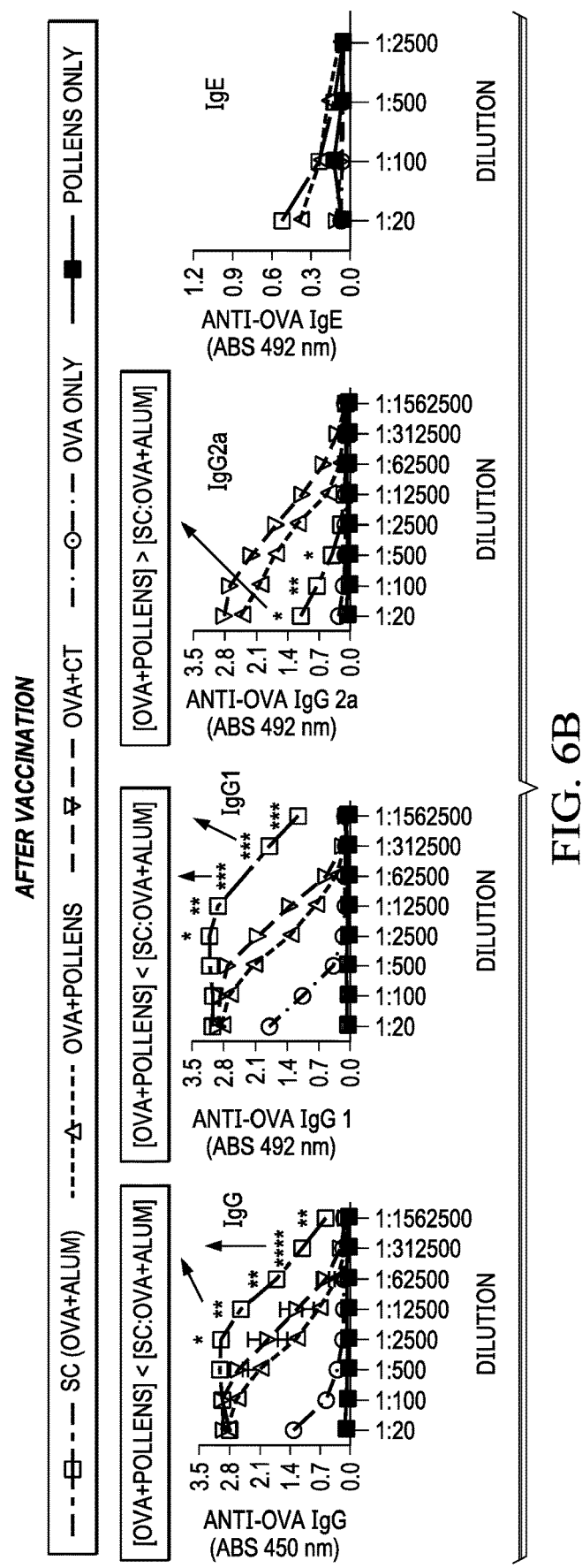
Figure 6C:
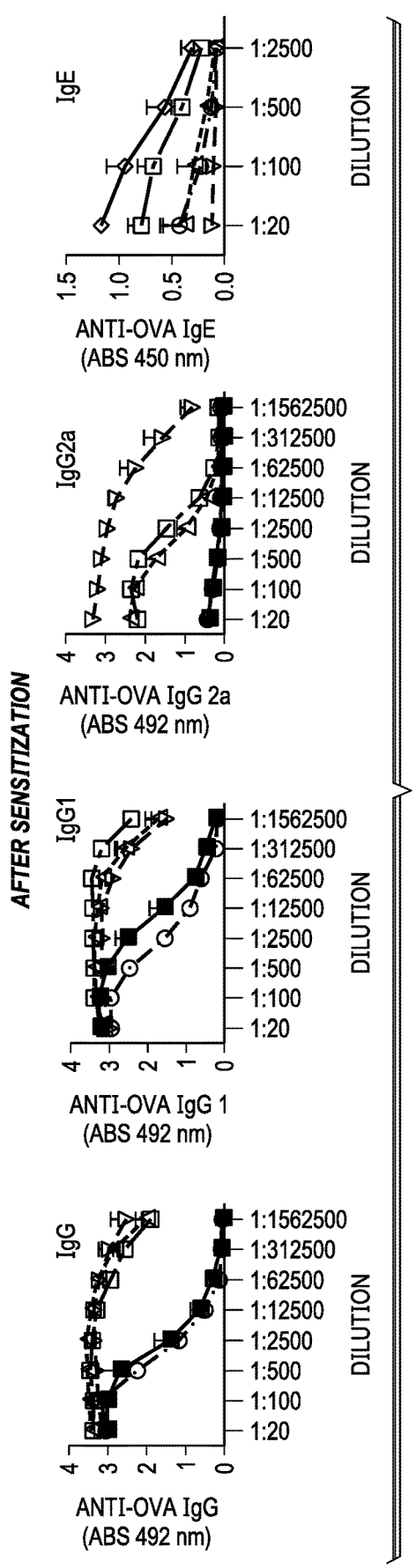
Figure 6D:
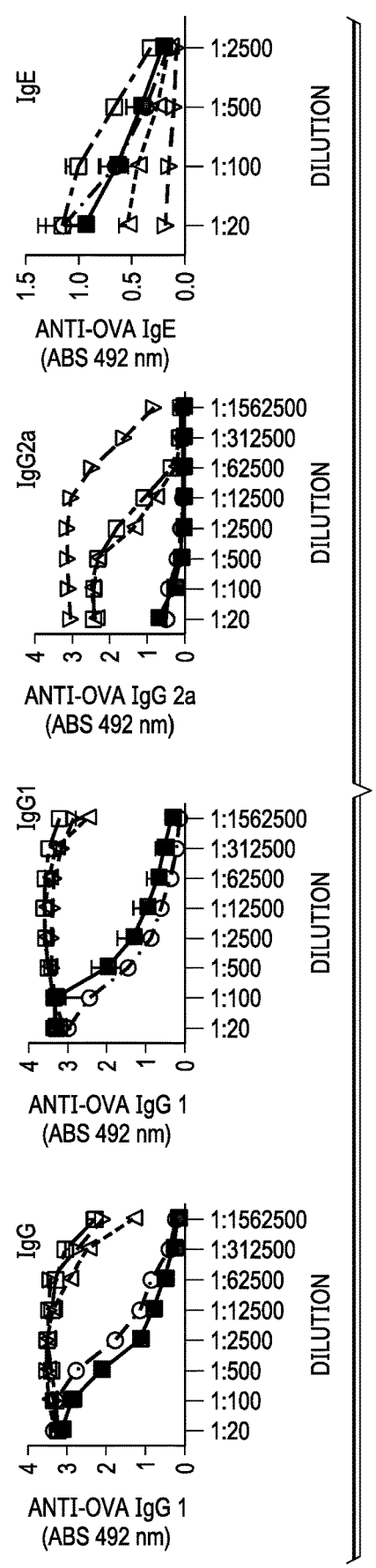
Figure 7A:
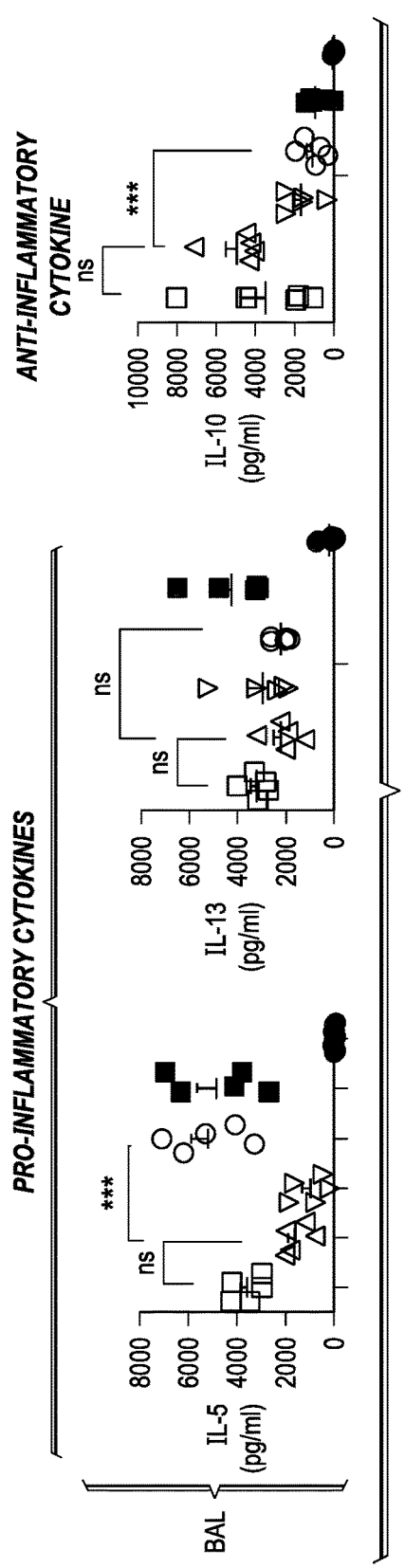
FIGS. 7A and 7B show Ova+pollen oral immunotherapy performs similar to subcutaneous (Sc) allergy shots in preventing allergy in a mouse model of Ova-respiratory allergy.
Figure 7B:
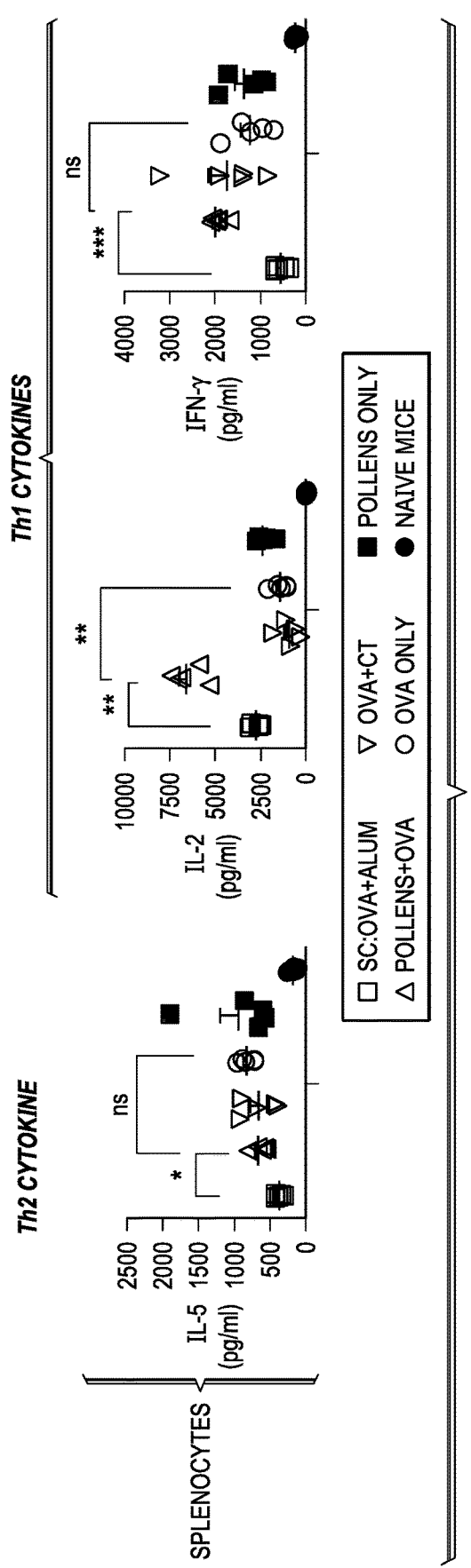

Oral-immunotherapy with pollen+allergen can 'prevent' development of airway allergy similar to the subcutaneous allergy shot. To validate the preventive efficacy of Ova+pollen oral immunotherapy, first mice were vaccinated with an oral dose of Ova+pollens weekly for eight weeks (FIG. 6A). As control groups, mice were given (i) subcutaneous injection of Ova (25 µg)+alum (250 µg) to mimic the conventional subcutaneous allergen immunotherapy (Sc) weekly for three weeks, (ii) oral Ova (100 µg)+CT (5 µg) given weekly for eight weeks, (iii) Ova alone (100 µg) given weekly for eight weeks, and (iv) pollens alone (5 mg) given weekly for eight weeks. Sensitized mice without any treatment and naïve mice (no exposure to OVA at all) were also used as control groups. Mice were then made allergic (also known as sensitized) to Ova by intraperitoneal (i.p.) injection of Ova+alum mixture (25 µg Ova+2 mg alum) (FIG. 6A). In this step, if vaccination has succeeded, the mice will not develop allergy to Ova. Allergen challenge: Mice were challenged with a high dose of Ova (50 µg Ova per mouse per day) through i.n. route for three consecutive days. If mice are sensitized, they will experience allergy symptoms after challenge. Anti-Ova IgG, IgG1, and IgG2a antibodies after vaccination were produced in the Ova+pollen group. While IgG and IgG1 was lower than the Sc group, the IgG2a was higher in Ova+pollen group. IgG2a stimulation is considered to be good for allergy treatment and prevention in mice, and points to the activation of Th1 pathway, which plays a significant role in suppression of airway inflammation (21) and food allergy (4). IgE levels were not significantly different between Ova+pollen and Sc groups. After sensitization and challenge, the levels of IgG, IgG1, IgG2a, and IgE for Ova+pollen and Sc groups were similar. After euthanasia, in the bronchoalvelar lavage (BAL), low expression of pro-inflammatory cytokine IL-5 was seen in Ova+pollens group in contrast to Ova alone group (FIG. 7A), which further indicates the prevention in airway inflammation when pollen is mixed with allergen in the formulation. No difference was seen between Ova+pollen and Sc groups. Interestingly, up-regulation of anti-inflammatory cytokine (IL-10) in Ova+pollen group indicates activation of T regulatory (Treg) cells. IL-10 cytokine is considered an anti-inflammatory cytokine expressed by T regulatory 1 (Treg1) cells, and it helps in suppression of airway inflammation (22), and regulates the expression of pro-inflammatory cytokines, and chemokines (23). Activation of Th1 pathway in Ova+pollen oral immunotherapy group was confirmed by high expression of Th1 cytokines in supernatant collected from splenocytes cultured in vitro under Ova re-stimulation. As seen in FIG. 7B, the expression of IL-2 and IFN-γ was significantly higher in Ova+pollens group than the Sc group.

Figure 8A:
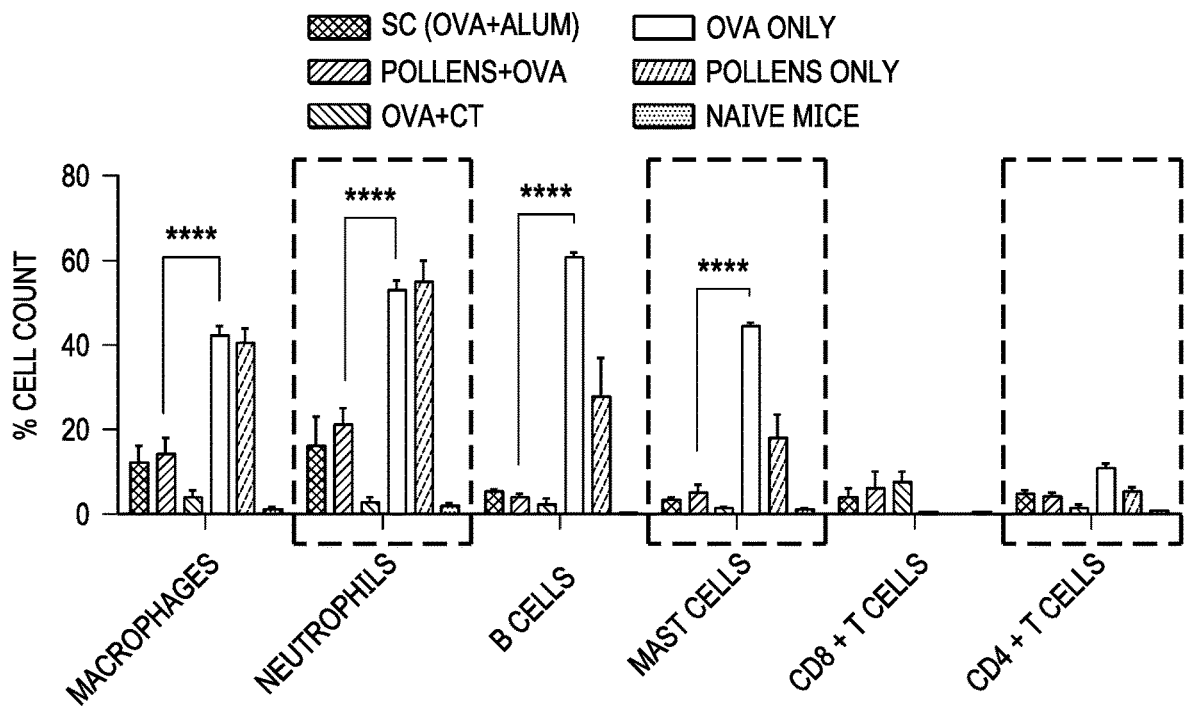
FIGS. 8A and 8B show Ova+pollen oral immunotherapy performs similar to Sc allergy shots in preventing allergy in a mouse model of Ova-respiratory allergy.
Figure 8B:
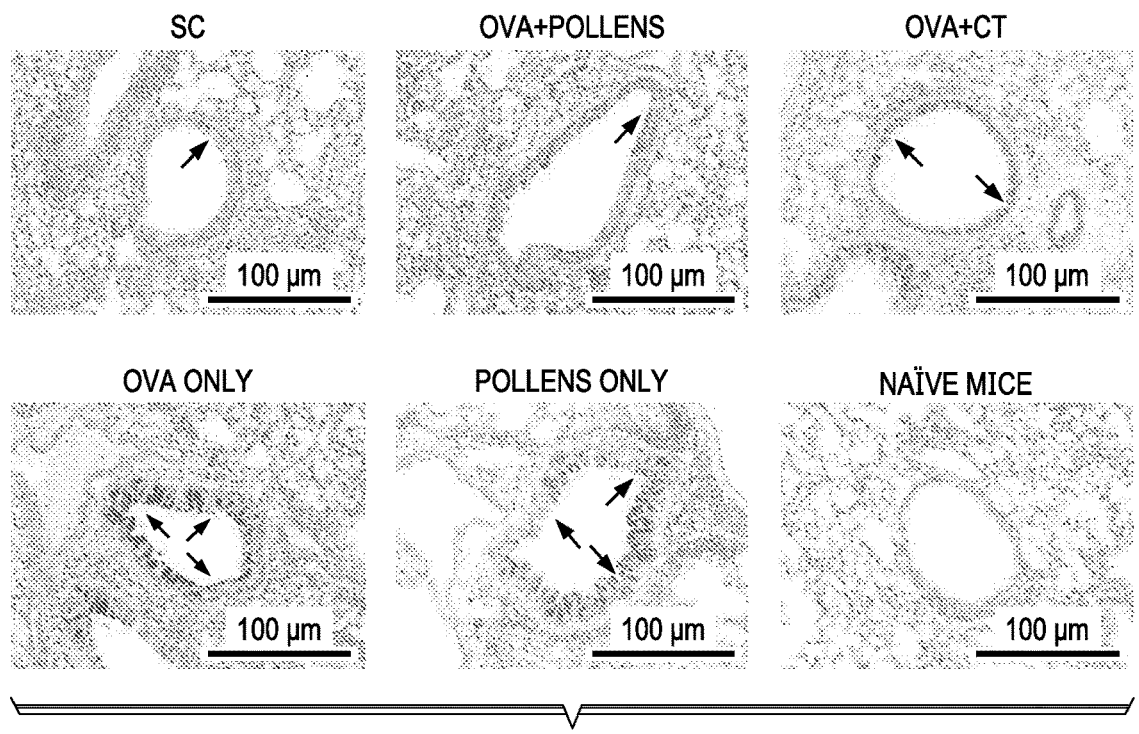

Pollen+allergen oral immunotherapy 'prevents' allergic airway inflammation similar to Sc shots. After euthanasia, in the BAL fluid infiltrating cell types were analyzed. Flow cytometry analysis (Attune NxT, Life Technologies, USA) showed a significantly ($p<0.05$) low percentage of neutrophil and macrophage cell counts in the Ova+pollens treated group as compared to Ova only group, but similar to Sc group (FIG. 8A). B and mast cells were significantly higher in the Ova alone group. No considerable differences were observed in CD4+ T and CD8+ T cells across all treatment groups. Further, lung tissues were fixed in formaldehyde, sectioned and stained with periodic-acid-Schiff (PAS) for mucus production. FIG. 8B shows that mucus production in Ova+pollens was negligible like the Sc group, but Ova alone group showed higher mucus production indicative of an inflammatory response.

Peanut extract+pollen generates a good antibody response. To demonstrate the ability of pollen to enhance immune response against a food allergen, the inventors formulated clean ragweed pollen with peanut extract (PE) and orally administered it to mice. Mice were fed with pollens (5 mg)+PE (100 µg) weekly for eight weeks, after which mice were bled to check anti-PE response (FIG. 9A). As seen with Ova, addition of ragweed pollen to PE led to significantly higher anti-PE IgG, IgG1, and IgG2a response than oral delivery of PE (100 µg) alone. Low PE specific IgE response was observed with PE+pollens group (FIG. 9B) indicating that ragweed pollen are safe because they do not cause peanut allergy in naïve mice.

Figure 10A:
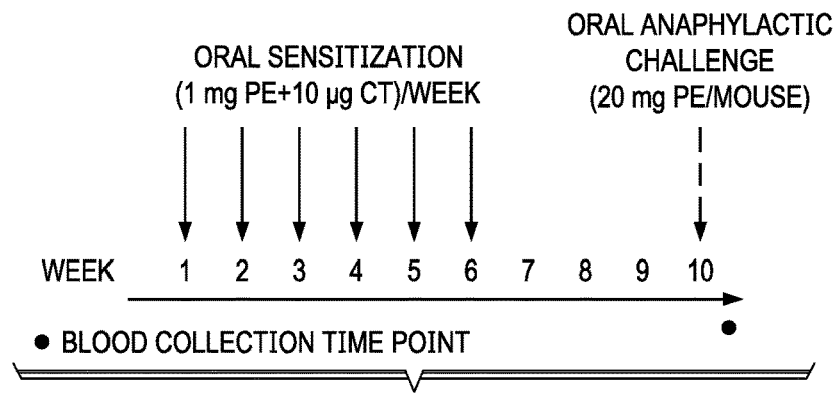
FIGS. 10A and 10B show the results in a peanut allergy mouse model using the present invention.
Figure 10B:
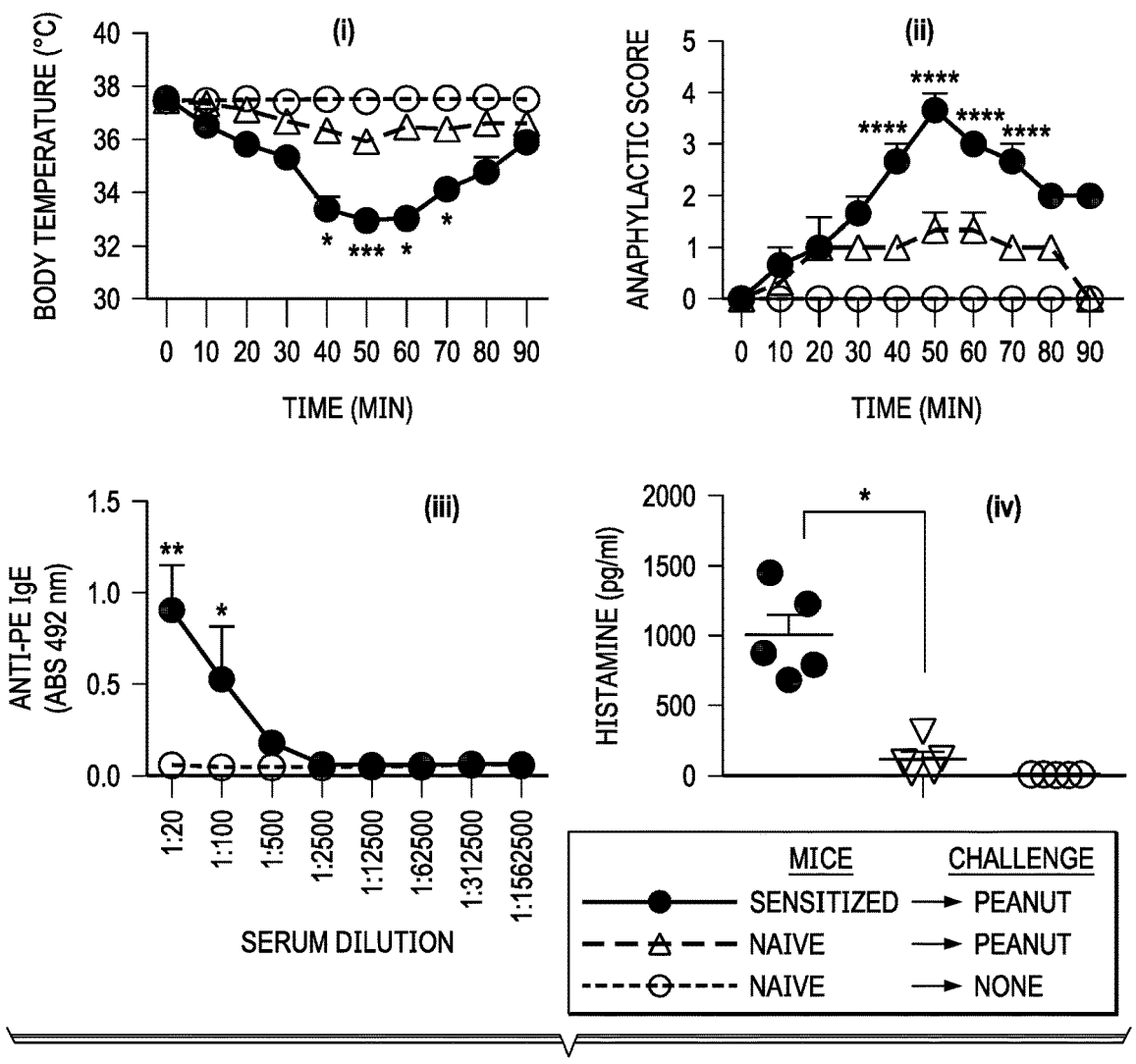

Peanut-allergy mouse model. Like the Ova-allergy respiratory model, to test efficacy of ragweed+PE in treating peanut allergy a mouse peanut allergy model was established. Mice were sensitized to peanut by feeding them 1 mg PE+10 µg CT weekly for six weeks (FIG. 10A). To check for allergic response, mice were challenged orally with 20 mg PE, and body temperature and clinical scores were recorded. As shown in FIG. 10B, drop in body temperature, and high anaphylactic score in sensitized mice in comparison to control naïve mice verified development of allergic reaction in sensitized mice. Five minutes post challenge, blood was also collected to analyze histamine and anti-PE IgE antibodies. Histamine is released by mast cells and basophils during an allergic reaction. An elevated level of histamine and IgE verified successful development of a mouse peanut allergy model. This model can be used to establish treatment and preventive capacity of pollen+PE, as was done for Ova+pollen.

Ragweed pollen are not toxic to Caco-2 cells and stimulate them to secrete proinflammatory cytokines. Human epithelial Caco-2 cells were cultured in trans well-inserts (FIG. 11A) for 22 days. Trans epithelial resistance was high confirming tight junction formation (FIG. 11B). At day 22 ragweed were added at different concentrations and the resistance continued to rise indicating that pollens did not disrupt tight junctions. As a control when EDTA was added, tight junctions were disrupted and within 1 h the resistance dropped. Cytotoxicity assay showed that ragweed and PLGA particles of similar size had similar toxicity levels (FIG. 11C). When Caco-2 cells were incubated with ragweed (2 mg/ml) proinflammatory cytokines were secreted by them (FIG. 11D).

Figure 12C:
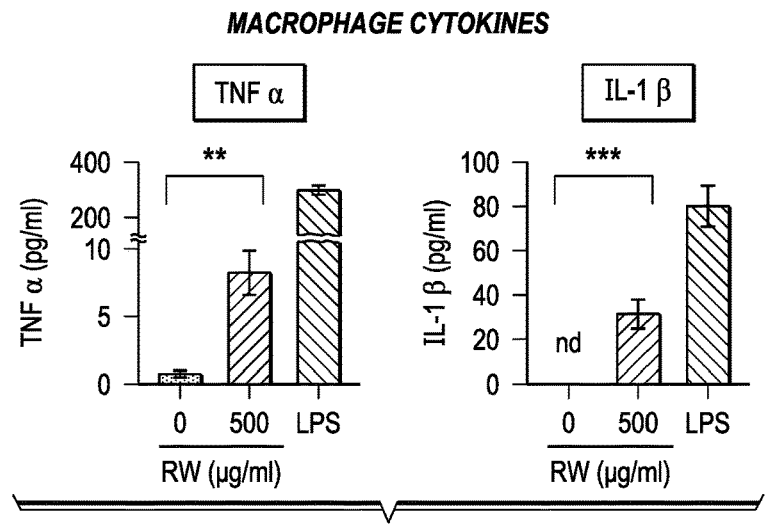
Figure 12D:
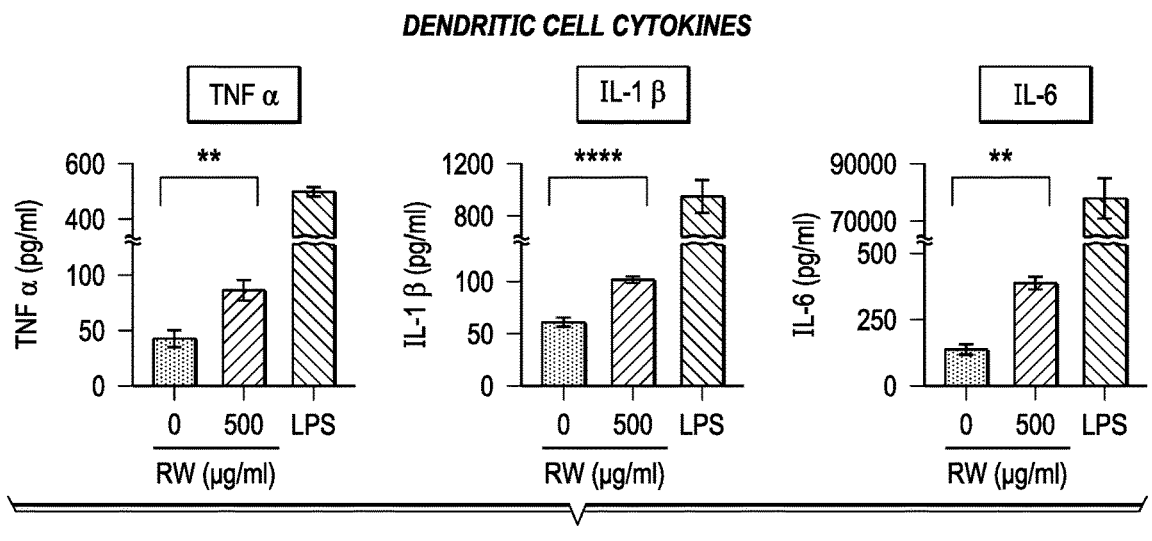
Figure 12E:
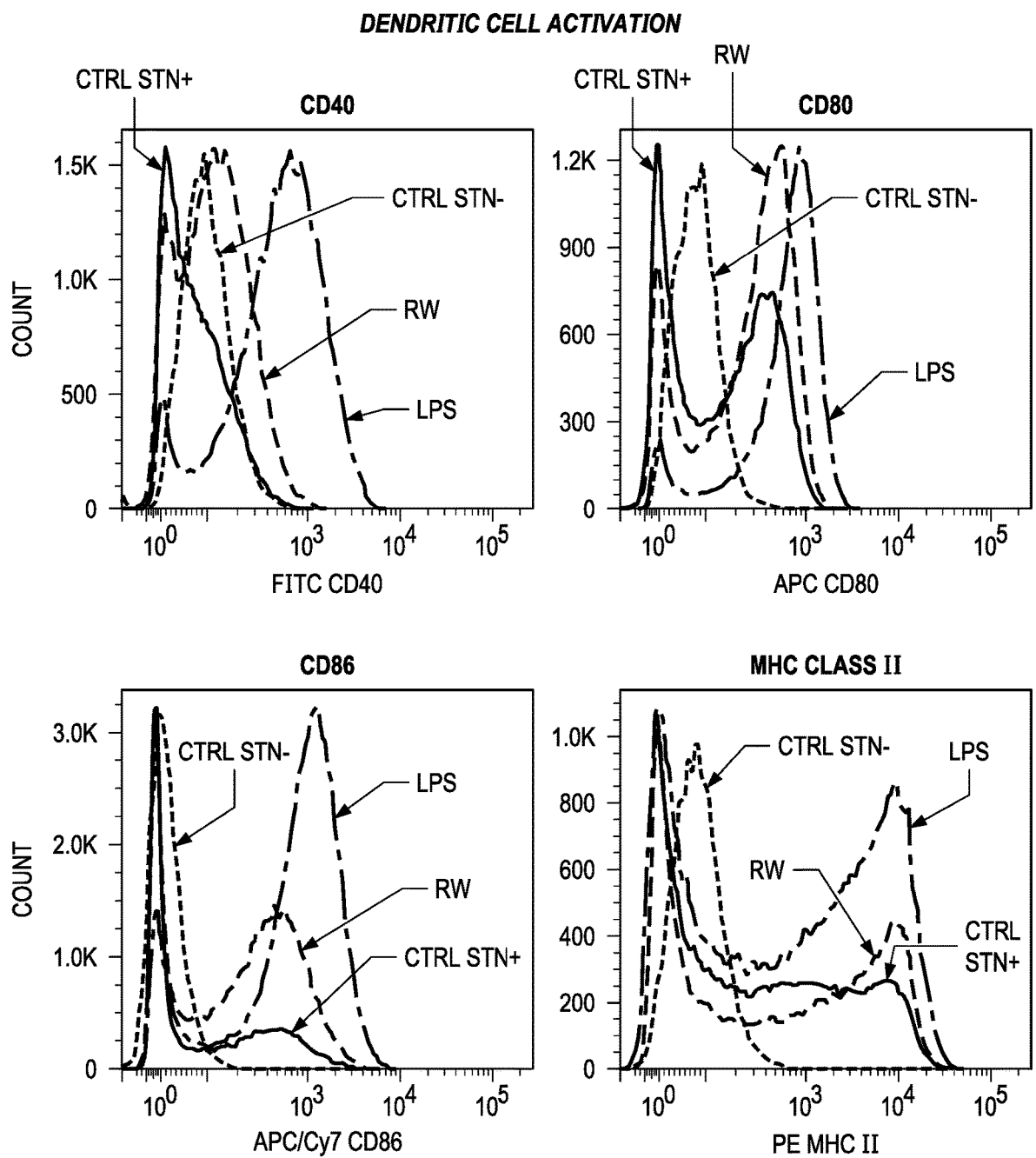

Ragweed pollen activate bone marrow derived macrophages and dendritic cells. The potential of pollen phagocytosis was examined by culturing them with macrophage cells (J774A.1). Macrophages attempted to phagocytose the pollen shells (FIG. 12A and FIG. 12B). Next, when dendritic cells and macrophages derived from the bone marrow cells of Balb/c mice were incubated with ragweed pollen, proinflammatory cytokines were secreted by both the cells (FIG. 12C and FIG. 12D). Further, it was seen that dendritic cells got activated when they were cultured in the presence of ragweed pollen (FIG. 12E).

Ragweed pollens adsorb antigen/allergen and cross the intestinal epithelium. When peanut extract was cultured with chemically cleaned ragweed pollen shells, it was found that protein was adsorbed on their surface (FIG. 13A). While a large part of the adsorbed protein could be removed by washing, some of it was still tightly adsorbed. This fraction could be seen on the protein gel when the pollens were treated in SDS buffer @95° C. 24 h after feeding the mice 5 mg ragweed, their intestine was cleaned, cut longitudinally, and viewed under a confocal microscope. Ragweed pollen could be seen in the wall tissue (FIG. 13B). Thorough washing and controls that the ragweed observed are indeed in the tissue were ensured.

It is contemplated that any embodiment discussed in this specification can be implemented with respect to any method, kit, reagent, or composition of the invention, and vice versa. Furthermore, compositions of the invention can be used to achieve methods of the invention.

It is understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it are apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

As regards the claims, each dependent claim can depend both from the independent claim and from each of the prior dependent claims for each and every claim so long as the prior claim provides a proper antecedent basis for a claim term or element.

REFERENCES IN BACKGROUND OF THE INVENTION

1. Chafen, J., S. J. Newberry, M. A. Riedl, and et al., Diagnosing and managing common food allergies: A systematic review. JAMA, 2010. 303(18): p. 1848-1856.
2. Nurmatov, U., I. Venderbosch, G. Devereux, F. E. Simons, and A. Sheikh, Allergen-specific oral immunotherapy for peanut allergy. Cochrane Database Syst Rev, 2012(9): p. CD009014.
3. Branum, A. M. and S. L. Lukacs, Food Allergy Among Children in the United States. Pediatrics, 2009. 124(6): p. 1549-1555.
4. Sicherer, S. H., A. Munoz-Furlong, J. H. Godbold, and H. A. Sampson, US prevalence of self-reported peanut, tree nut, and sesame allergy: 11-year follow-up. Journal of Allergy and Clinical Immunology, 2010. 125(6): p. 1322-1326.
5. Hourihane, J. O. B., S. A. Roberts, and J. O. Warner, Resolution of peanut allergy: case-control study. BMJ: British Medical Journal, 1998. 316(7140): p. 1271-1275.
6. Skolnick, H. S., M. K. Conover-Walker, C. B. Koerner, H. A. Sampson, W. Burks, and R. A. Wood, The natural history of peanut allergy. Journal of Allergy and Clinical Immunology, 2001. 107(2): p. 367-374.
7. Fleischer, D. M., M. K. Conover-Walker, L. Christie, A. W. Burks, and R. A. Wood, The natural progression of peanut allergy: Resolution and the possibility of recurrence. Journal of Allergy and Clinical Immunology, 2003. 112(1): p. 183-189.
8. Oppenheimer, J. J., H. S. Nelson, S. A. Bock, F. Christensen, and D. Y. Leung, Treatment of peanut allergy with rush immunotherapy. J Allergy Clin Immunol, 1992. 90(2): p. 256-62.
9. Nelson, H. S., J. Lahr, R. Rule, A. Bock, and D. Leung, Treatment of anaphylactic sensitivity to peanuts by immunotherapy with injections of aqueous peanut extract. J Allergy Clin Immunol, 1997. 99(6 Pt 1): p. 744-51.
10. NIAID-Sponsored Expert Panel, J. A. Boyce, A. Assa'ad, A. W. Burks, S. M. Jones, H. A. Sampson, R. A. Wood, M. Plaut, S. F. Cooper, M. J. Fenton, S. H. Arshad, S. L. Bahna, L. A. Beck, C. Byrd-Bredbenner, C. A. Camargo, Jr., L. Eichenfield, G. T. Furuta, J. M. Hanifin, C. Jones, M. Kraft, B. D. Levy, P. Lieberman, S. Luccioli, K. M. McCall, L. C. Schneider, R. A. Simon, F. E. Simons, S. J. Teach, B. P. Yawn, and J. M. Schwaninger, Guidelines for the diagnosis and management of food allergy in the United States: report of the NIAID-sponsored expert panel. J Allergy Clin Immunol, 2010. 126(6 Suppl.): p. S1-58.
11. Bollinger, M. E., L. M. Dahlquist, K. Mudd, C. Sonntag, L. Dillinger, and K. McKenna, The impact of food allergy on the daily activities of children and their families. Annals of Allergy, Asthma & Immunology, 2006. 96(3): p. 415-421.
12. Walkner, M., C. Warren, and R. S. Gupta, Quality of Life in Food Allergy Patients and Their Families. Pediatric Clinics of North America, 2015. 62(6): p. 1453-1461.
13. Meyer, R., C. De Koker, R. Dziubak, C. Venter, G. Dominguez-Ortega, R. Cutts, N. Yerlett, A. K. Skrapak, A. T. Fox, and N. Shah, Malnutrition in children with food allergies in the UK. Journal of Human Nutrition and Dietetics, 2014. 27(3): p. 227-235.
14. Mehta, H., M. Groetch, and J. Wang, Growth and Nutritional Concerns in Children with Food Allergy. Current opinion in allergy and clinical immunology, 2013. 13(3): p. 275-279.
15. Diesner, S. C., E. Untersmayr, P. Pietschmann, and E. Jensen-Jarolim, Food Allergy: Only a Pediatric Disease? Gerontology, 2011. 57(1): p. 28-32.
16. Wohrl, S. and G. Sting, Underestimation of allergies in elderly patients. Lancet, 2004. 363(9404): p. 249.
17. Sampson, H. A., S. Aceves, S. A. Bock, J. James, S. Jones, D. Lang, K. Nadeau, A. Nowak-Wegrzyn, J. Oppenheimer, T. T. Perry, C. Randolph, S. H. Sicherer, R. A. Simon, B. P. Vickery, R. Wood, P. Joint Task Force on Practice, D. Bernstein, J. Blessing-Moore, D. Khan, D. Lang, R. Nicklas, J. Oppenheimer, J. Portnoy, C. Randolph, D. Schuller, S. Spector, S. A. Tilles, D. Wallace, W. Practice Parameter, H. A. Sampson, S. Aceves, S. A. Bock, J. James, S. Jones, D. Lang, K. Nadeau, A. Nowak-Wegrzyn, J. Oppenheimer, T. T. Perry, C. Randolph, S. H. Sicherer, R. A. Simon, B. P. Vickery, and R. Wood, Food allergy: a practice parameter update-2014. J Allergy Clin Immunol, 2014. 134(5): p. 1016-25 e43.
18. Pajno, G. B., L. Cox, L. Caminiti, V. Ramistella, and G. Crisafulli, Oral Immunotherapy for Treatment of Immunoglobulin E-Mediated Food Allergy: The Transition to Clinical Practice. Pediatric Allergy, Immunology, and Pulmonology, 2014. 27(2): p. 42-50.
19. Wood, R A., Food allergen immunotherapy: Current status and prospects for the future. J Allergy Clin Immunol, 2016. 137(4): p. 973-82.
20. Hofmann, A. M., A. M. Scurlock, S. M. Jones, K. P. Palmer, Y. Lokhnygina, P. H. Steele, J. Kamilaris, and A. W. Burks, Safety of a peanut oral immunotherapy protocol in children with peanut allergy. J Allergy Clin Immunol, 2009. 124(2): p. 286-91, 291.e1-6.
21. Jones, S. M., L. Pons, J. L. Roberts, A. M. Scurlock, T. T. Perry, M. Kulis, W. G. Shreffler, P. Steele, K. A. Henry, M. Adair, J. M. Francis, S. Durham, B. P. Vickery, X. Zhong, and A. W. Burks, Clinical efficacy and immune regulation with peanut oral immunotherapy. Journal of Allergy and Clinical Immunology, 2009. 124(2): p. 292-300.e97.
22. Deol, S. and J. A. Bird, Current opinion and review on peanut oral immunotherapy. Hum Vaccin Immunother, 2014. 10(10): p. 3017-21.
23. Sampson, H. A., Peanut Oral Immunotherapy: Is It Ready for Clinical Practice? The Journal of Allergy and Clinical Immunology: In Practice, 2013. 1(1): p. 15-21.
24. Vickery, B. P., J. P. Berglund, C. M. Burk, J. P. Fine, E. H. Kim, J. I. Kim, C. A. Keet, M. Kulis, K. G. Orgel, R. Guo, P. H. Steele, Y. V. Virkud, P. Ye, B. L. Wright, R A. Wood, and A. W. Burks, Early oral immunotherapy in peanut-allergic preschool children is safe and highly effective. J Allergy Clin Immunol, 2017. 139(1): p. 173-181 e8.
25. Blumchen, K., H. Ulbricht, U. Staden, K. Dobberstein, J. Beschorner, L. C. L. de Oliveira, W. G. Shreffler, H. A. Sampson, B. Niggemann, U. Wahn, and K. Beyer, Oral peanut immunotherapy in children with peanut anaphylaxis. Journal of Allergy and Clinical Immunology, 2010. 126(1): p. 83-91.e1.
26. Narisety, S. D., P. A. Frischmeyer-Guerrerio, C. A. Keet, M. Gorelik, J. Schroeder, R. G. Hamilton, and R.A. Wood, A randomized, double-blind, placebo-controlled pilot study of sub/ingua/versus oral immunotherapy for the treatment of peanut allergy. Journal of Allergy and Clinical Immunology, 2015. 135(5): p. 1275-1282.e6.
27. Anagnostou, K., A. Clark, Y. King, S. Islam, J. Deighton, and P. Ewan, Efficacy and safety of high-dose peanut oral immunotherapy with factors predicting outcome. Clinical & Experimental Allergy, 2011. 41(9): p. 1273-1281.
28. Anagnostou, K., S. Islam, Y. King, L. Foley, L. Pasea, S. Bond, C. Palmer, J. Deighton, P. Ewan, and A. Clark, Assessing the efficacy of oral immunotherapy for the desensitisation of peanut allergy in children (STOP II): a phase 2 randomised controlled trial. The Lancet. 383 (9925): p. 1297-1304.
29. D. E. Campbell, S. Mehr, Fifty years of allergy: 1965-2015, J Paediatr Child Health, 51 (2015) 91-93.
30. T. A. Platts-Mills, The allergy epidemics: 1870-2010, J Allergy Clin Immunol, 136 (2015) 3-13.
31. S. J. Galli, M. Tsai, IgE and mast cells in allergic disease, Nat Med, 18 (2012) 693-704.
32. G. D'Amato, A. Stanziola, A. Sanduzzi, G. Liccardi, A. Salzillo, C. Vitale, A. Molino, A. Vatrella, M. D'Amato, Treating severe allergic asthma with anti-IgE monoclonal antibody (omalizumab): a review, Multidiscip Respir Med, 9 (2014) 23.
33. R. M. Naclerio, The effect of antihistamines on the immediate allergic response: a comparative review, Otolaryngol Head Neck Surg, 108 (1993) 723-730.
34. A. J. Frew, Allergen immunotherapy, J Allergy Clin Immunol, 125 (2010) S306-313.
35. H. Fujita, M. B. Soyka, M. Akdis, C. A. Akdis, Mechanisms of allergen-specific immunotherapy, Clin Transl Allergy, 2 (2012) 2.
36. R. Valenta, R. Campana, K. Marth, M. van Hage, Allergen-specific immunotherapy: from therapeutic vaccines to prophylactic approaches, J Intern Med, 272 (2012) 144-157.
37. S. C. Bukantz, A. S. Bagg, R. F. Lockey, Adverse effects and fatalities associated with subcutaneous allergen immunotherapy, Clin Allergy Immunol, 21 (2008) 455-468.
38. C. Incorvaia, Preventive capacity of allergen immunotherapy on the natural history of allergy, J Prev Med Hyg, 54 (2013) 71-74.
39. J. N. Larsen, L. Broge, H. Jacobi, Allergy immunotherapy: the future of allergy treatment, Drug Discov Today, 21 (2016) 26-37.
40. Z. Zolkipli, G. Roberts, V. Cornelius, B. Clayton, S. Pearson, L. Michaelis, R. Djukanovic, R. Kurukulaaratchy, S. H. Arshad, Randomized controlled trial of primary prevention of atopy using house dust mite allergen oral immunotherapy in early childhood, J Allergy Clin Immunol, 136 (2015) 1541-1547 e1541-1511.
41. L. Jacobsen, B. Niggemann, S. Dreborg, H. A. Ferdousi, S. Halken, A. Host, A. Koivikko, L. A. Norberg, E. Valovirta, U. Wahn, C. Moller, Specific immunotherapy has long-term preventive effect of seasonal and perennial asthma: 10-year follow-up on the PAT study, Allergy, 62 (2007) 943-948.
42. E. Valovirta, A. K. Berstad, J. de Blic, A. Bufe, P. Eng, S. Halken, P. Ojeda, G. Roberts, P. Tommerup, E. M. Varga, I. Winnergard, G. A. P. investigators, Design and recruitment for the GAP trial, investigating the preventive effect on asthma development of an SQ-standardized grass allergy immunotherapy tablet in children with grass pollen-induced allergic rhinoconjunctivitis, Clin Ther, 33 (2011) 1537-1546.
43. L. Cox, H. Nelson, R. Lockey, C. Calabria, T. Chacko, I. Finegold, M. Nelson, R. Weber, D. I. Bernstein, J. Blessing-Moore, D. A. Khan, D. M. Lang, R. A. Nicklas, J. Oppenheimer, J. M. Portnoy, C. Randolph, D. E. Schuller, S. L. Spector, S. Tilles, D. Wallace, Allergen immunotherapy: a practice parameter third update, J Allergy Clin Immunol, 127 (2011) 51-55.
44. W. Li, Z. Zhang, A. Saxon, K. Zhang, Prevention of oral food allergy sensitization via skin application of food allergen in a mouse model, Allergy, 67 (2012) 622-629.
45. H. J. Lee, N. R. Lee, B. K. Kim, M. Jung, D. H. Kim, C. S. Moniaga, K. Kabashima, E. H. Choi, Acidification of stratum corneum prevents the progression from atopic dermatitis to respiratory allergy, Exp. Dermatol., (2016).
46. M. Hessenberger, R. Weiss, E. E. Weinberger, C. Boehler, J. Thalhamer, S. Scheiblhofer, Transcutaneous delivery of CpG-adjuvanted allergen via laser-generated micropores, Vaccine, 31 (2013) 3427-3434.
47. S. J. Kim, J. H. Shin, S. C. Kim, C. K. Park, S. W. Kim, Preventive effects of oral tolerance on allergic inflammation and airway remodeling in a murine model, Am. J. Rhinol. Allergy, 27 (2013) ell-16.
48. P. G. Holt, P. D. Sly, H. A. Sampson, P. Robinson, R. Loh, H. Lowenstein, A. Calatroni, P. Sayre, Prophylactic use of sublingual allergen immunotherapy in high-risk children: a pilot study, J. Allergy Clin. Immunol., 132 (2013) 991-993 e991.
49. C. Incorvaia, S. Masieri, P. Berto, S. Scurati, F. Frati, Specific immunotherapy by the sublingual route for respiratory allergy, Allergy Asthma Clin. Immunol., 6 (2010) 29.
50. Taylor et al. (2004). Clin Exp. Allergy 34, pp. 689-695.
51. Allergen Nomenclature Sub-Committee of the International Union of Immunological Societies (Zhou et al. (2013). International Journal of Food Science, V. 2013, Article ID 909140.
52. Sicherer et al. (1998). Pediatrics 102(1), p. e6.
53. Sicherer et al. (2000). Allergy 55(6), pp. 515-521.
54. de Leon et al. (2003). Clin. Exp. Allergy 33(9), pp. 1273-1280.
55. Rosenfeld et al. (2012).

REFERENCES IN BRIEF DESCRIPTION OF THE DRAWINGS

1. Shivanna, K. R., Pollen Biology and Biotechnology 2003, Enfield, N. H., USA: Science Publishers.
2. Wittborn, J., K. V. Rao, G. El-Ghazaly, and J. R. Rowley, Substructure of spore and pollen grain exines in Lycopodium, A/nus, Betu/a, Fagus and Rhododendron—Investigation with Atomic Force and Scanning Tunnelling Microscopy. Grana, 1996. 35(4): p. 185-198.
3. Wittborn, J., K. V. Rao, G. El-Ghazaly, and J. R. Rowley, Nanoscale Similarities in the Substructure of the Exines of Fagus pollen grains and lycopodium spores. Annals of Botany, 1998. 82(2): p. 141-145.
4. Atwe, S. U., Y. Ma, and H. S. Gill, Pollen grains for oral vaccination. J Control Release, 2014. 194: p. 45-52.
5. Diego-Taboada, A., S. T. Beckett, S. L. Atkin, and G. Mackenzie, Hollow pollen shells to enhance drug delivery. Pharmaceutics, 2014. 6(1): p. 80-96.

6. Jorde, W. and H. F. Linskens, Zur Persorption Von Pollen and Spoken Durch die Intake Darmschleimhaut. Allergy, 1974. 29(3): p. 165-175.
7. Volkheimer, G., Passage of particles through the wall of the gastrointestinal tract. Environ Health Perspect, 1974. 9: p. 215-25.
8. Volkheimer, G., F. H. Schulz, A. Lindenau, and U. Beitz, Persorption of metallic iron particles. Gut, 1969. 10(1): p. 32-3.
9. Du, Y. Z. and M. Kodaka, Preparation and characterization of biotinylated and enzyme-immobilized heterobifunctional latex particles as nanobio devices. Journal of Polymer Science Part A: Polymer Chemistry, 2005. 43(3): p. 562-574.
10. Taudorf, E., L. C. Laursen, A. Lanner, B. Bjorksten, S. Dreborg, M. Soborg, and B. Weeke, Oral immunotherapy in birch pollen hay fever. J Allergy Clin Immunol, 1987. 80(2): p. 153-61.
11. Taudorf, E., L. C. Laursen, R. Djurup, E. Kappelgaard, C. T. Pedersen, M. Soborg, P. Wilkinson, and B. Weeke, Oral administration of grass pollen to hay fever patients. An efficacy study in oral hyposensitization. Allergy, 1985. 40(5): p. 321-35.

REFERENCES IN DETAILED DESCRIPTION OF THE INVENTION

1. Sicherer, S. H., A. Munoz-Furlong, J. H. Godbold, and H. A. Sampson, US prevalence of self-reported peanut, tree nut, and sesame allergy: 11-year follow-up. Journal of Allergy and Clinical Immunology, 2010. 125(6): p. 1322-1326.
2. Oppenheimer, J. J., H. S. Nelson, S. A. Bock, F. Christensen, and D. Y. Leung, Treatment of peanut allergy with rush immunotherapy. J Allergy Clin Immunol, 1992. 90(2): p. 256-62.
3. Nelson, H. S., J. Lahr, R. Rule, A. Bock, and D. Leung, Treatment of anaphylactic sensitivity to peanuts by immunotherapy with injections of aqueous peanut extract. J Allergy Clin Immunol, 1997. 99(6 Pt 1): p. 744-51.
4. Wood, R A., Oral Immunotherapy for Food Allergy. J Investig Allergol Clin Immunol, 2017: p. 0.
5. Kanaoka, M. M. and T. Higashiyama, Peptide signaling in pollen tube guidance. Current Opinion in Plant Biology, 2015. 28: p. 127-136.
6. Heslop-Harrison, Y. and J. Heslop-Harrison, Structural and functional variation in pollen intines, in Pollen and Spores, S. Blackmore and S. Barnes, Editors. 1991, Clarendon Press: Oxford. p. 331-343.
7. Shaw, G., The chemistry of sporopollenin, in Sporopollenin, P. R. Grant, M. Muir, P. V. Gijzel, and G. Shaw, Editors. 1971, Academic Press, London.
8. Shivanna, K R., Pollen Biology and Biotechnology 2003, Enfield, N. H., USA: Science Publishers.
9. Wittborn, J., K. V. Rao, G. El-Ghazaly, and J. R. Rowley, Substructure of spore and pollen grain exines in Lycopodium, A/nus, Betu/a, Fagus and Rhododendron—Investigation with Atomic Force and Scanning Tunnelling Microscopy. Grana, 1996. 35(4): p. 185-198.
10. Wittborn, J., K. V. Rao, G. El-Ghazaly, and J. R. Rowley, Nanoscale Similarities in the Substructure of the Exines of Fagus pollen grains and lycopodium spores. Annals of Botany, 1998. 82(2): p. 141-145.
11. Atwe, S. U., Y. Ma, and H. S. Gill, Pollen grains for oral vaccination. J Control Release, 2014. 194: p. 45-52.
12. Diego-Taboada, A., S. T. Beckett, S. L. Atkin, and G. Mackenzie, Hollow pollen shells to enhance drug delivery. Pharmaceutics, 2014. 6(1): p. 80-96.
13. Jorde, W. and H. F. Linskens, Zur Persorption Von Pollen and Spoken Durch die Intake Darmschleimhaut. Allergy, 1974. 29(3): p. 165-175.
14. Volkheimer, G., Passage of particles through the wall of the gastrointestinal tract. Environ Health Perspect, 1974. 9: p. 215-25.
15. Volkheimer, G., F. H. Schulz, A. Lindenau, and U. Beitz, Persorption of metallic iron particles. Gut, 1969. 10(1): p. 32-3.
16. Du, Y. Z. and M. Kodaka, Preparation and characterization of biotinylated and enzyme-immobilized heterobifunctional latex particles as nanobio devices. Journal of Polymer Science Part A: Polymer Chemistry, 2005. 43(3): p. 562-574.
17. Kim, J., J. W. Grate, and P. Wang, Nanostructures for enzyme stabilization. Chemical Engineering Science, 2006. 61(3): p. 1017-1026.
18. Bernstein, T. B. and S. M. Feinberg, Oral ragweed pollen therapy clinical results of experiments on gastrointestinal absorption. Arch Intern Med (Chic), 1938. 62(2): p. 297-304.
19. Feinberg, S. M., F. L. Foran, M. R. Lichtenstein, E. Padnos, B. Z. Rappaport, J. Sheldon, and M. Zeller, ORAL POLLEN THERAPY IN RAGWEED POLL/NOSIS A COOPERATIVE STUDY. The Journal of the American Medical Association, 1940. 115(1): p. 23-29.
20. Richert, J. H., Failure to Develop Saecoidosis after the Oral Ingestion of Pine Pollen. American Review of Respiratory Disease, 1959. 80(5): p. 760.
21. Akdis, C. A. and M. Akdis, Mechanisms of allergen-specific immunotherapy. J Allergy Clin Immunol, 2011. 127(1): p. 18-27; quiz 28-9.
22. Akdis, C. A. and M. Akdis, Mechanisms of immune tolerance to allergens: role of/L-10 and Tregs. J Clin Invest, 2014. 124(11): p. 4678-80.
23. O'Garra, A., P. L. Vieira, P. Vieira, and A. E. Goldfeld, IL-10-producing and naturally occurring CD4+ Tregs: limiting collateral damage. J Clin Invest, 2004. 114(10): p. 1372-8.

What is claimed is:

1. A composition for the oral delivery of a therapeutic agent that reduces or desensitizes food, respiratory or other allergies, comprising:
   a pollen cleaned to remove naturally-occurring allergic plant proteins; and
   a therapeutically effective amount of an allergen loaded into the cleaned pollen, wherein the allergen is in an amount that enhances the production of antibodies against the allergen, wherein the allergen is in, on, or coated on the cleaned pollen or a combination thereof, and the cleaned pollen is a cleaned ragweed pollen.

2. The composition of claim 1, wherein the cleaned pollen is stabilized during processing or storage in a vehicle, or both, or the cleaned pollen is an adjuvant.

3. The composition of claim 1, wherein the composition is adapted to treat an allergy by immunotherapy.

4. The composition of claim 1, wherein the allergen is a food allergy allergen to selected from a groundnut, peanut, milk, egg, tree nut, seed, fish, shellfish, crustacean, cereal, legume allergy, hazelnut, cashew, walnut, pecan, brazil nut, macadamia, chestnut, pistachio, coconut, almond, sesame, soy, kidney bean, black bean, common bean, chickpea, pea, cow pea, lentil or lupin allergy or a mustard seed allergy, or a combination thereof.

5. The composition of claim 1, wherein the allergen is peanut allergen that comprises Ara h1, Ara h2, Ara h3, Ara h4, Ara h5, Ara h6, Ara h7, Ara h8, Ara h9, Ara h10, Ara h11, Ara h12, Ara h13, a peptide fragment thereof, or a combination thereof.

6. The composition of claim 1, wherein the allergen is a portion of a plant, animal, arthropod, insect, fungus, or venom allergen, an aeroallergen, pollen allergen, animal allergen, dust mite allergen, cockroach allergen, or mold or fungi allergen, Hymenoptera allergen, or combinations thereof, or an extract derived from the allergic source material, or purified from the extract, or synthesized chemically or biologically, and a fragment thereof of the allergen that will fit within the cleaned pollen.

7. The composition of claim 1, wherein the allergen can be a mixture of two or more allergens in a ratio from 0.001:100 to 100:0.001.

8. The composition of claim 1, wherein the amount of the allergen loaded into the cleaned pollen in an amount that is below the threshold that triggers an allergic response to the allergen.

9. The composition of claim 1, wherein an opening in the cleaned pollen is at least partially or fully closed with a biodegradable polymer.

10. The composition of claim 1, further comprising one or more adjuvants in any size, shape, form or physical state introduced in, on, or coated on the cleaned pollen or a combination thereof to improve the immune response against the allergen.

11. The composition of claim 1, wherein the allergen is provided amount is less than about 1 gram, less than about 100 mg, less than about 1 mg, less than about 500 microgram, and less than about 100 microgram, between 1 nanogram to 1 gram per dose, about 1 grams per dose, more preferably about 500 mg per dose, about 100 mg per dose, about 10 mg per dose, or less than 10 mg per dose.

12. The composition of claim 1, wherein the composition has improved organoleptic properties when compared to allergen alone.

13. The composition of claim 1, wherein a desensitization in a subject to the allergen is by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, about 70%, about 75%, at least about 80%, at least about 85%, or at least about 90%, wherein the percent is determined from at least one of: an increase in cytokine production of IL-10, TGF-β, or both; increase production of IgG allergen-specific antibodies; decreased number of mast cells; decreased number of basophils, or a combination thereof, as compared to not receiving the treatment.

14. A method for making a composition for delivery of a therapeutic agent that reduces or desensitizes food, respiratory or other allergies, the composition comprising:

cleaning a pollen to remove naturally-occurring allergic protein or fragment thereof to form a cleaned pollen, wherein the cleaned pollen is ragweed;

loading a therapeutically effective amount of an allergen in the cleaned pollen wherein the allergen is in and/or on the cleaned pollen; and providing to a subject in need of immunotolerance with a therapeutically effective amount of the allergen in or on the cleaned pollen sufficient to induce immune tolerance to the allergen, wherein the allergen is a peanut allergen that comprises Ara h1, Ara h2, Ara h3, Ara h4, Ara h5, Ara h6, Ara h7, Ara h8, Ara h9, Ara h10, Ara h11, Ara h12, Ara h13, a peptide fragment thereof, or a combination thereof.

15. The method of claim 14, further comprising the step of stabilizing the composition during processing for storage.

16. The method of claim 14, further comprising adapting the composition to treat an allergy.

17. The method of claim 14, further comprising the step of adapting the composition for oral, subcutaneous, intranasal, or intrapulmonary administration.

18. The composition of claim 1, wherein the allergen is provided amount is less than about 1 gram, less than about 100 mg, less than about 1 mg, less than about 500 microgram, and less than about 100 microgram, between 1 nanogram to 1 gram per dose, about 1 grams per dose, more preferably about 500 mg per dose, about 100 mg per dose, about 10 mg per dose, or less than 10 mg per dose.

19. The method of claim 14, wherein a desensitization to the allergen is by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, about 70%, about 75%, at least about 80%, at least about 85%, or at least about 90%, wherein the percent is determined from at least one of: an increase in cytokine production of IL-10, TGF-β, or both; increase production of IgG allergen-specific antibodies; decreased number of mast cells; decreased number of basophils, or a combination thereof, as compared to not receiving the treatment.

20. A method for oral delivery of an allergen for reducing, desensitizing, or treating an allergic reaction to the allergen, comprising:

identifying a subject in need of reducing an allergic reaction to the allergen;

cleaning a pollen to remove naturally-occurring allergic plant proteins to form a cleaned pollen;

loading a therapeutically effective amount of an allergen in and/or on the cleaned pollen, wherein the cleaned pollen is ragweed; and providing orally to a subject in need of immunotolerance with a therapeutically effective amount of the allergen in or on the cleaned pollen sufficient to induce immune tolerance to the allergen.

21. The method of claim 20, wherein a desensitization to the allergen is by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, about 70%, about 75%, at least about 80%, at least about 85%, or at least about 90%, wherein the percent is determined from at least one of: an increase in cytokine production of IL-10, TGF-β, or both; increase production of IgG allergen-specific antibodies; decreased number of mast cells; decreased number of basophils, or a combination thereof, as compared to not receiving the treatment.

22. The method of claim 20, wherein the subject is from about 2 years old to about 12 years old, about 3 years old to about 12 years old, about 4 years old to about 12 years old, about 4 years old to about 11 years old, about 4 years old to about 10 years old, or about 2 years old to about 9 years old, or greater than about 12 years old.

23. The method of claim 20, wherein a sustained unresponsiveness lasts for about 1 month, about 2 months, about 3 months, about 4 months, about 5 months, about 6 months, about 7 months, about 8 months, about 9 months, about 10 months, about 11 months, about 12 months, or greater than about 12 months after therapy has ended.

24. The method of claim 20, wherein dosing is carried out at a frequency, repetition, and duration that leads to desensitization to the allergen.

25. The method of claim 24, wherein a frequency of administration is selected from: at least once a day, at least more than once a day, about 10 times a day, about 30 times a day, about every other day, about every 3 days, about every 7 days, about every 14 days, about every 21 days, about every 30 days, about every 2 months, about every 3 months, about every 4 months, about every 6 months, about every 1 year, and each dose could be the same or it could be different.

* * * * *